US005800386A

United States Patent [19]

Bellifemine

[11] Patent Number: 5,800,386
[45] Date of Patent: Sep. 1, 1998

[54] DEVICE FOR MONITORING AND CONTROLLING AN INTRAVENOUS INFUSION SYSTEM

[76] Inventor: Francesco Bellifemine, Via Perla 57, Varese, Italy

[21] Appl. No.: 559,839

[22] Filed: Nov. 20, 1995

[30]  Foreign Application Priority Data

Nov. 25, 1994 [IT] Italy ................................. MI94A2396

[51] Int. Cl.$^6$ ............................................. A61M 1/00
[52] U.S. Cl. ........................................................ 604/65
[58] Field of Search ........................... 604/65–67, 30–34, 604/49–50, 118, 151, 246–247

Primary Examiner—Manuel Mendez
Attorney, Agent, or Firm—Diller, Ramik & Wight, PC

[57]  ABSTRACT

A device for monitoring and controlling an intravenous infusion system includes a storage battery within a housing defining a drip chamber from which an intravenous infusion tube emerges which can be regulated by a shutoff device. The shutoff device is defined by first and second levers biased by respective first and second springs which are tripped through a microcontroller circuit responding to droplet sensing.

43 Claims, 26 Drawing Sheets

DEVICE FOR MONITORING AND CONTROLLING AN INTRAVENOUS INFUSION SYSTEM

BACKGROUND OF THE INVENTION

This invention relates to a device for monitoring and controlling an intravenous infusion system, which is of low electricity consumption and of tendentiously small longitudinal and transverse overall dimensions.

Intravenous infusion systems used in hospitals or at home by patients have to be continuously monitored by the nursing personnel or the patient to check that the administration rate remains within the defined limits characteristic of each medicament and to detect any interruption or depletion of the solution. This is necessary to avoid annoying consequences such as useless prolongation of the time for which the medicament is administered, or unpleasant effects on the patient, such as air entry into the system, back flow of blood along the system tube, or dangerous overdosage of the medicament.

Devices are already known for performing these monitoring and control functions. For example, U.S. Pat. No. 5,088,990 in the name of Hivale describes an apparatus consisting of two plastics containers comprising in one side a cavity arranged to internally embrace the drip chamber. It is provided with a photosensor for sensing the passage of droplets within the drip chamber, and an electronic alarm circuit comprising a warning horn and a warning lamp which operate if infusion of the solution droplets is interrupted or slows down excessively.

However this apparatus is arranged only to give an optical-acoustic alarm indication, without being able to sense an increase in infusion rate or to shut off solution flow in the case of defects.

Its application is also relatively burdensome, because it involves placing the two containers adjacent to the system drip chamber so that they surround part of it, and each time adjusting the opening of the compartment in relation to the chamber diameter. Finally, the current consumption of this device is such as to make its reduction desirable in order to limit the volume of the set of electrical storage batteries and hence of the device itself. It is also known to use improved forms of this device, such as that described in U.S. Pat. No. 5 439 442 of Aug. 8, 1995 in the name of the present patentee. Besides performing the same functions as the preceding, this apparatus also shuts off the flow of the medicament if the administration rate of the medicament exceeds a certain limiting value and/or if the infusion solution is depleted.

When the apparatus sound an alarm, the shutoff device closes a spring-loaded gripper jaw by releasing the gripper jaw by means of an electromagnet. Hence the starting force required to operate the mechanism can be tendentiously high, especially if the electrical storage batteries are at low charge.

A further device disclosed in U.S. Pat. No. 5 439 442 comprises a circuit which on receiving information from a bar code reader operates a geared motor capable of appropriately regulatory the delivery of the medicament by acting more or less directly on the exit tube by means of a cam. However this device presents two problems which it would be desirable to eliminate. Firstly, although the bar code reading system is very useful particularly in the case of repeated infusions of different medicaments (and hence requiring different infusion rates) in the patient's home, the apparatus requires the user hospital to be provided with further equipment capable of printing the bar code on appropriate labels. In addition, as the cam operates directly on the tube axis, a motor of relatively high torque is required, resulting in increased dimensions and energy consumption.

BRIEF SUMMARY OF THE INVENTION

An object of the present invention is to solve the aforesaid problems by providing a device for monitoring and controlling an intravenous infusion system which is of tendentiously low electricity consumption and hence of small overall size.

By interrupting the operation of the sensor means during a second time interval included within the time interval between the passage of two successive droplets, the device achieves a substantial saving in the electrical energy provided by the set of storage batteries. Consequently for equal electrical storage battery capacity, the device can operate without interruption for a longer time. Alternatively for a given operating time between charges, the device can use a set of storage batteries having a lesser volume.

The fact that the device comprises a pre-alarm threshold (during which the shutoff device does not act, although the warning means operate) means that those ignorable operating abnormalities which usually precede those requiring urgent action by nursing personnel can be detected.

Again, the fact of not interrupting administration during the pre-alarm period avoids unwelcome extension of the medicament infusion time, while aiding the nursing personnel which hence have a longer time available for action before the shutoff device interrupts administration of the medicament.

Further objects, characteristics and advantages of the present invention will be apparent from the detailed description given hereinafter and from the accompanying drawings, which are provided by way of non-limiting example and in which:

DETAILED DESCRIPTION OF THE INVENTION

Figure 4:
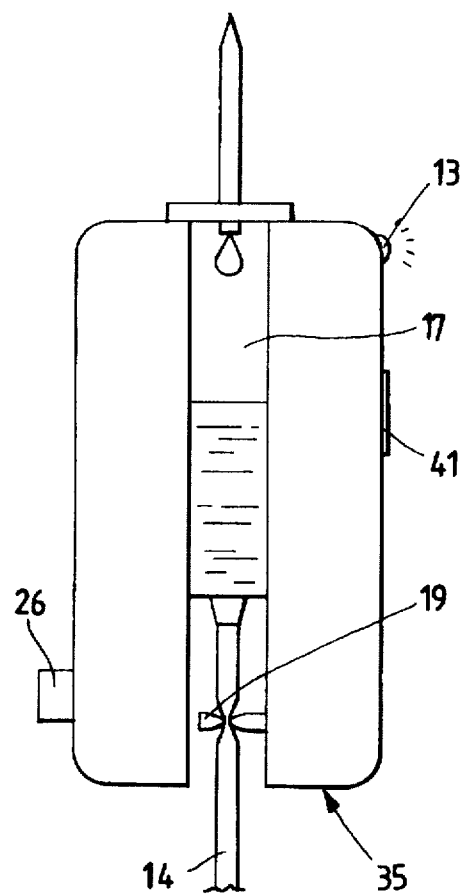
FIG. 4 is a schematic view of the device of the invention applied to the exit tube of an intravenous infusion system.

A monitoring and control device 1 of the invention includes a set of electrical storage batteries 2, comprising three 1.2 volt nickel/cadmium batteries rechargeable either by a conventional external battery charger or a dedicated one (not shown), connected to the device 1 via a socket 35 (FIGS. 4 and 5) through a hole formed in the bottom of the device container.

A housing 3 is provided in the interior of the container and can be closed about a drip chamber 17 (FIG. 4) of the intravenous infusion system, and means 4 (FIGS. 1–4) is provided for shutting off the system liquid flow. The housing 3 is preferably constructed of dark coloured or opaque material in order to absorb light originating from the external environment and prevent interference with sensor devices 28 and 29 contained in the housing 3.

A first, a second and a third compartment 15, 16 and 18, respectively, house all the components of the present invention which are grouped within a single plastic container of such dimensions as to be of small overall size while at the same time embracing a relatively large number of functions and being practical in use.

Two holes 10, 11 are provided through the constituent plastic material of the walls of the housing 3. In an embedded position in correspondence with the two holes 10, 11 there are inserted respectively an infrared emitter diode 28 and a receiver photodiode 29, which can sense the passage of liquid droplets within the drip chamber 17.

The infrared emitter diode 28 emits a beam in a direction perpendicular to the vertical trajectory of the droplets. An interruption in the passage of this beam indicates the fall of a solution droplet.

The beam is reflected by a concave mirror 30 (FIG. 1) located on the opposite side of the housing 3 across from the infrared emitter diode 28 and the receiver photo diode 29 in a position perpendicular to the emitted beam and within a cavity 31 the purpose of which is to protect the sensing system from light infiltration from the external environment. The particular shape of the mirror 30 means that all the rays emitted and reflected converge into a single region, in which the receiver photodiode 29 in located.

This arrangement is very advantageous compared with the known arrangement of locating the emitter diode 28 and the receiver photodiode 29 in coaxial positions on opposite sides of the vertical axis representing the droplet trajectory. In this manner, with the single addition of the concave mirror 4 of relatively low cost, being of the adhesive film type, two beams are obtained in practice, which being slightly diverging cover a greater area than a single beam, with greater probability of intercepting the droplet, even if this should fall outside the central axis of the drip chamber 17, this occurring for example if this latter is inclined because of possible imperfect positioning of the bottle in its support. Moreover, one and the same electronic circuit card 12 can be used for positioning, the two sensor elements 28 and 29, with the result of being able to substantially simplify and automate the assembly of the entire electronic components on the circuit card or circuit board 12.

The electronic circuit board 12 operating and controlling the device 1 mainly comprises an oscillator 21 and a microcontroller 40. The reference numeral 13 indicates a two-colour LED pilot lamp for indicating system operation or abnormalities, 33 indicates an acoustic emergency alarm (typically a piezoelectric buzzer), and 28 and 29 indicate the infrared emitter diode and the receiver diode, respectively.

A reed switch 48, suitably connected into the electronic circuit 12, forms together with a knob 41 a switch for activating the device 1.

An electrolytic capacitor 37 which is charged on activating the device 1, stores a certain quantity of energy for use by the electronic circuit 12 should the feed voltage be reduced, this occurring in particular at the moment in which the electromagnet 5 is energized.

Figure 1:
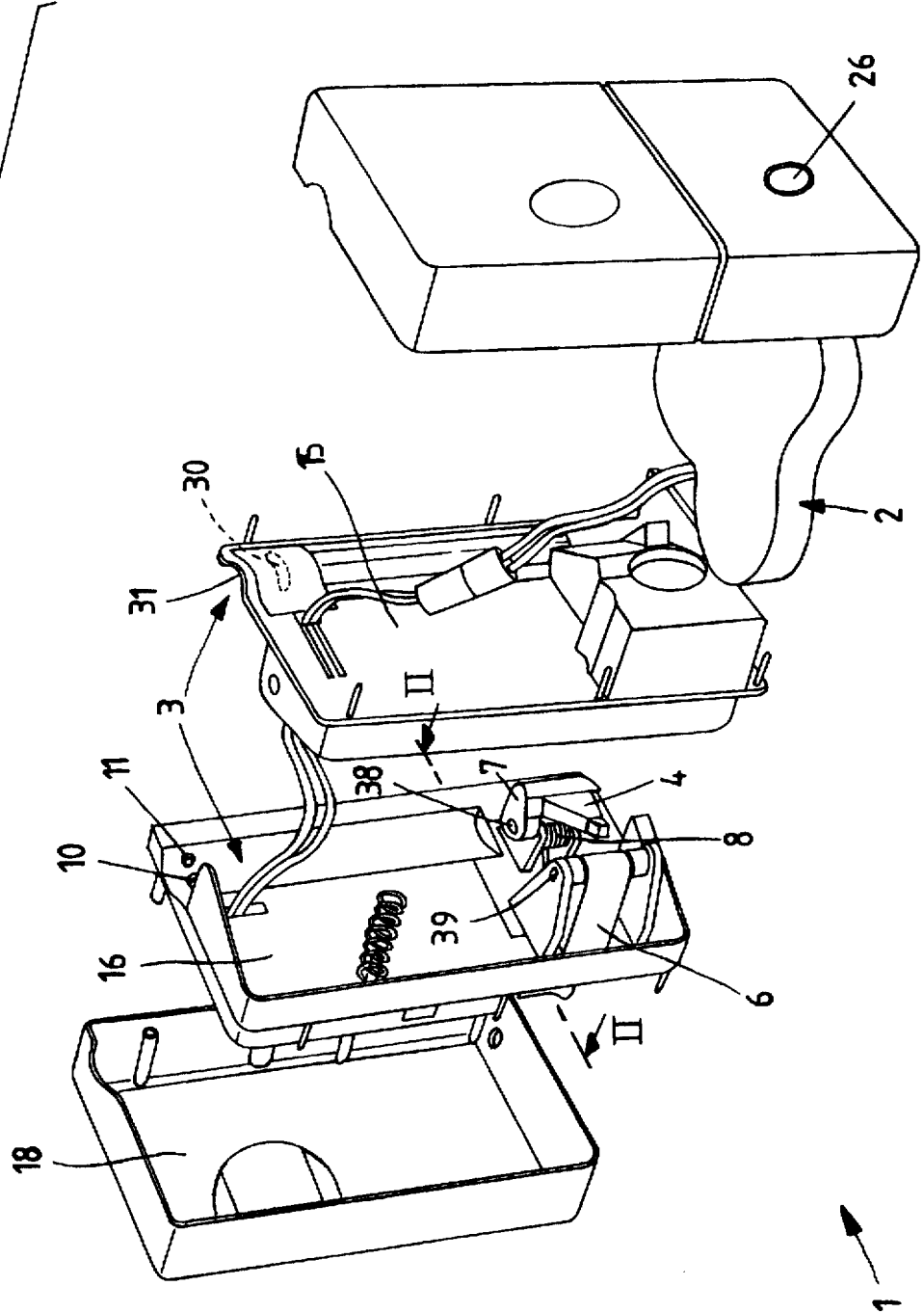
FIG. 1 is a schematic exploded perspective view of a first embodiment of the device according to the present invention.
Figure 2:
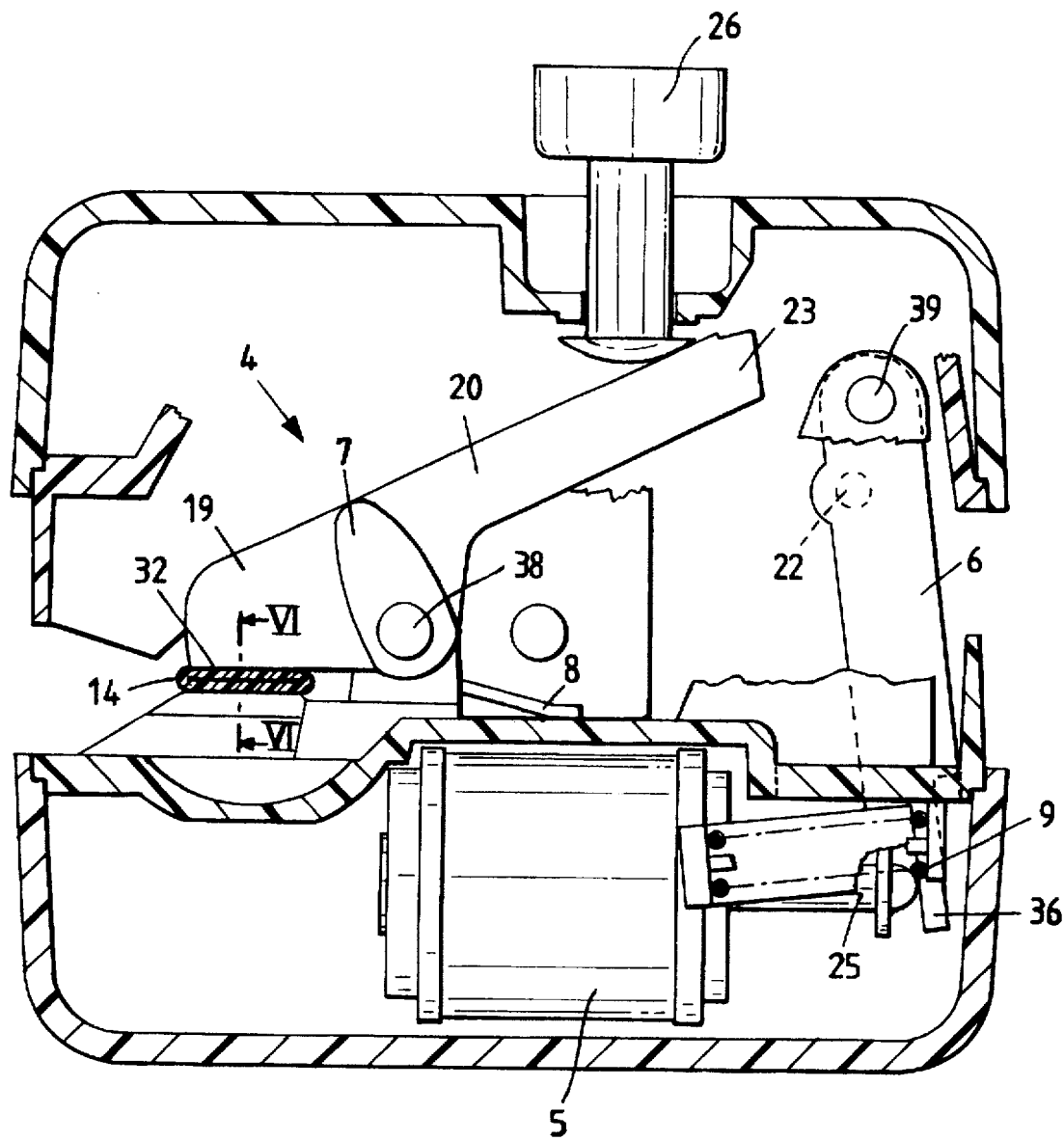
FIG. 2 is a section through the device on the line II—II of FIG. 1 at the moment in which the shutoff device throttles the tube of the system.
Figure 6:
FIG. 6 is a schematic section through the shutoff device of FIG. 2 taken on the line VI—VI.
Figure 3:
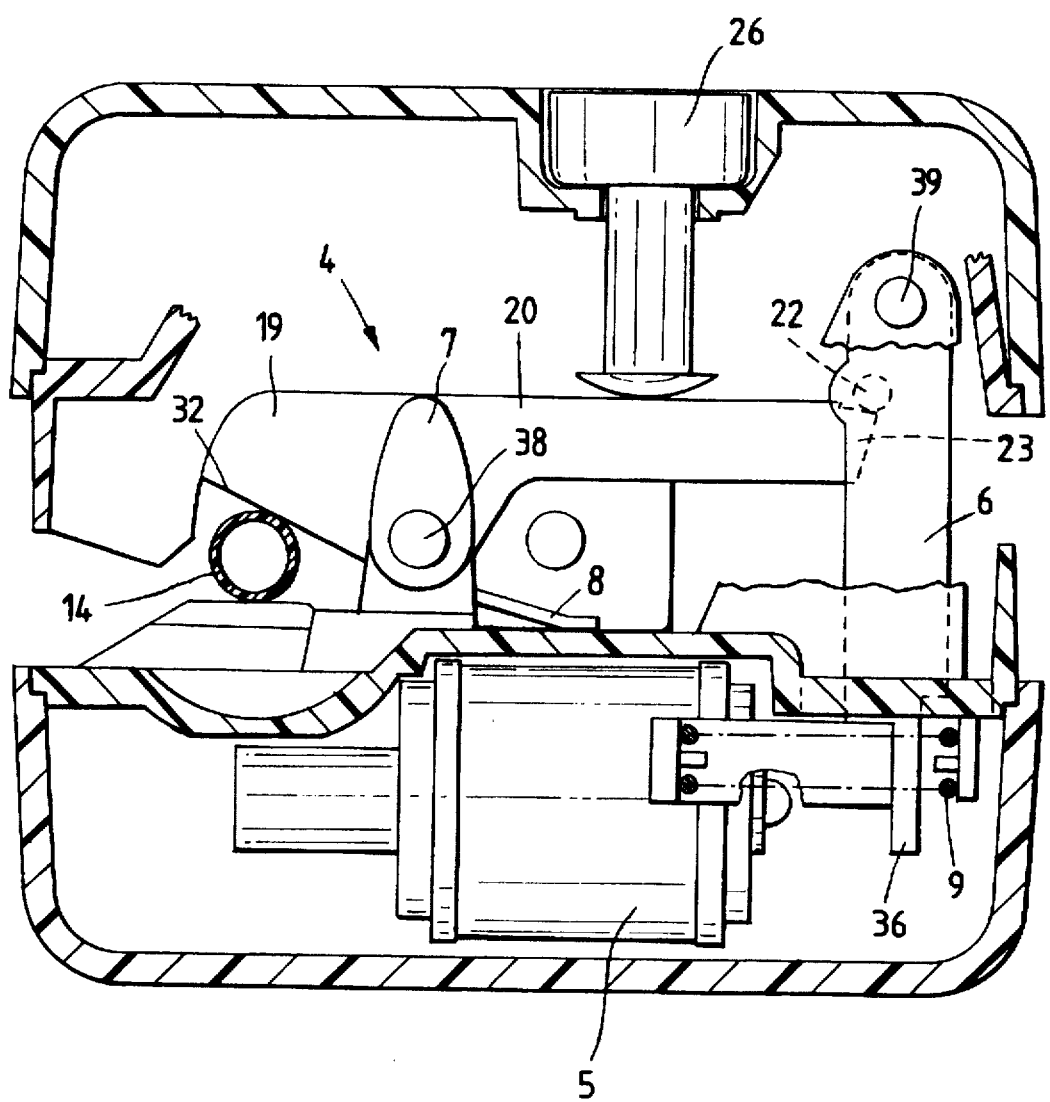
FIG. 3 again shows a section through the device on the line II—II of FIG. 1, but with the shutoff device in its preloaded position.

As can be seen in particular from FIGS. 2 and 3, the liquid flow shutoff device 4 consists of a first trip lever 6, a second shutoff lever 7 which throttles the tube 14, a torsion spring 8 acting on the lever 7, a compression spring 9 which maintains the lever 6 in position, a pushbutton 26 which resets the system, and an electromagnet 5 which trips the linkage.

The main part of the shutoff device 4 is the shutoff lever 7, which is urged to the close-off position of FIG. 2 by the spring 8. Said lever 7 has a short arm 19, of about 7 mm in length, an end 32 of which has a shape such as to easily throttle the system tube 14, and a long arm 20 of at least 16 mm in length.

For increased reliability of operation, the electromagnet 5 is powered with three successive currant pulses lasting a few tenths of a second, at a voltage of about 3.6 volts, with a current consumption of about 400 mA. It hence operates pulse-wise to ensure effective trip action, and generates a force of about 0.07–0.08 newtons on a rod 25.

Hence for a relatively small electricity consumption, a throttling action on the tube 14 is obtained which is particularly effective and advantageous in relation to the applied force. This is achieved by virtue of the combination of the springs 8 and 9 and the structural characteristics of the shutoff lever 7 and trip lever 6, which are first class levers and hence of advantageous type. In this respect, a fulcrum 38 of the shutoff lever 7 is located closer to the point at which the force is applied to the tube 14 than the point at which the external force is applied by the user via the pushbutton 26, and in addition a counteracting pin 22 positioned on the trip lever 6, into which the end 23 of the shutoff lever 7 is inserted during the pre-loading stage, is provided in proximity to the point of application of this pre-loading force, at a distance of about ⅕ of the total length of the lever. On the end distant from said point of application there acts the electromagnet 5, against which said trip lever 6 is maintained, urged by the spring 9.

This system is able to apply a throttling force of about 20 newtons to the tube 14. The torsion spring 8 applies a force only slightly greater than 20 newtons when maintained in its pre-load position.

When the electromagnet 5 is energized, its rod 25 pushes against the end of the trip lever 6 which in moving also moves the position of the pin 22, to release the end 23 of the shutoff lever 7, this latter then throttling the tube 14 by means of its end 32. The system is then reset on withdrawing the device 1 from the drip chamber 17, by pressing the pushbutton 26 as far as it goes, to rehook the end 23 of the shutoff lever 7 under the pin 22, while at the same time releasing the tube 14 and enabling the intravenous infusion system to be disengaged from the device 1, which is hence mechanically ready for subsequent use on another intravenous infusion system. When the device 1 trips, the pushbutton 26 is forced outwards and projects from the container, so giving visual indication that tripping has occurred.

A permanent magnet 27 (FIG. 5) draws the rod 25 (forming the moving core of the electromagnet 5) into its retracted position (FIG. 3) within the electromagnet 5 after each current. Because of the particular position of the permanent magnet 27 relative to the electromagnet 5 and rod 25, its pulling action on the rod 25 is a minimum on impact of the rod 25 against the trip lever 6 and is a maximum when said rod 25 is in the opposite position.

Figure 5:
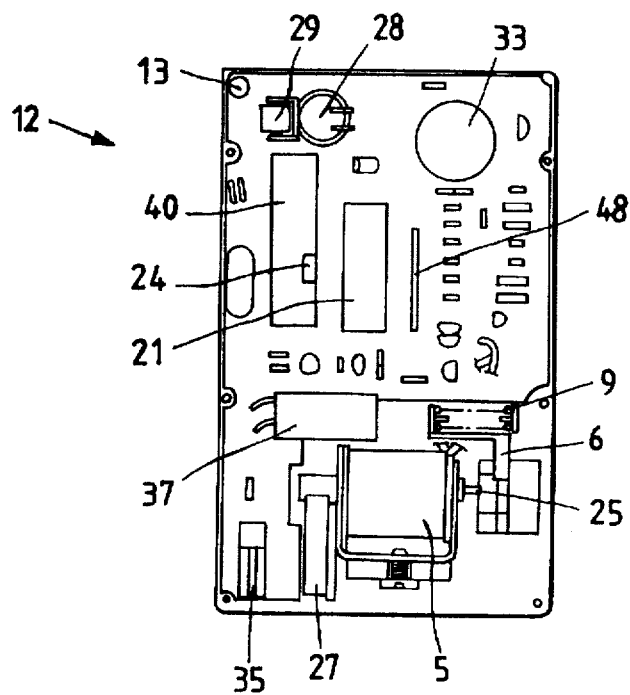
FIG. 5 is a schematic plan view of a first embodiment of the electronic circuit contained within one of the compartments of the device.
Figure 7A:
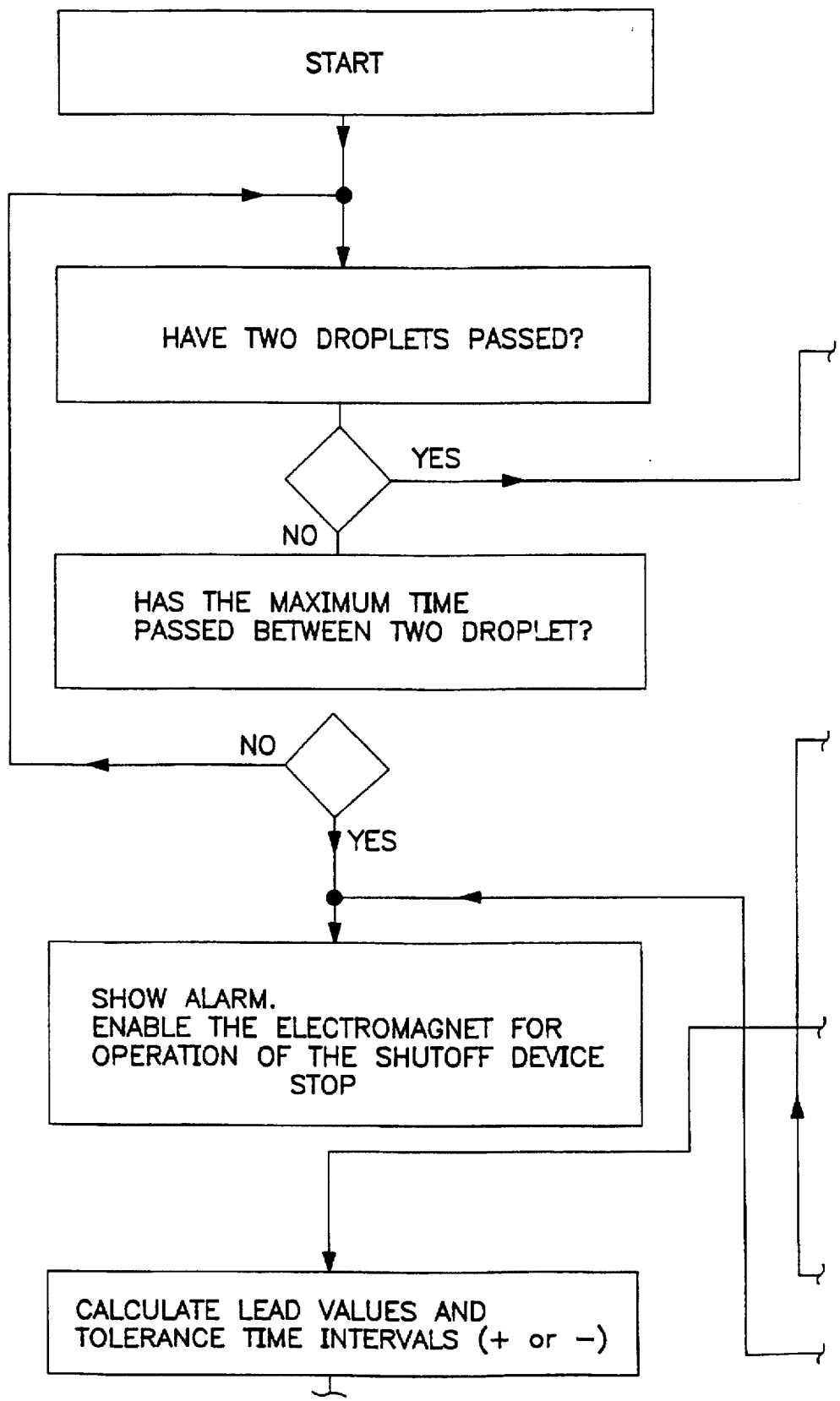
FIG. 7 is a schematic flow diagram corresponding to the operation of the first embodiment of the device electronic circuit of the present invention.
Figure 7B:
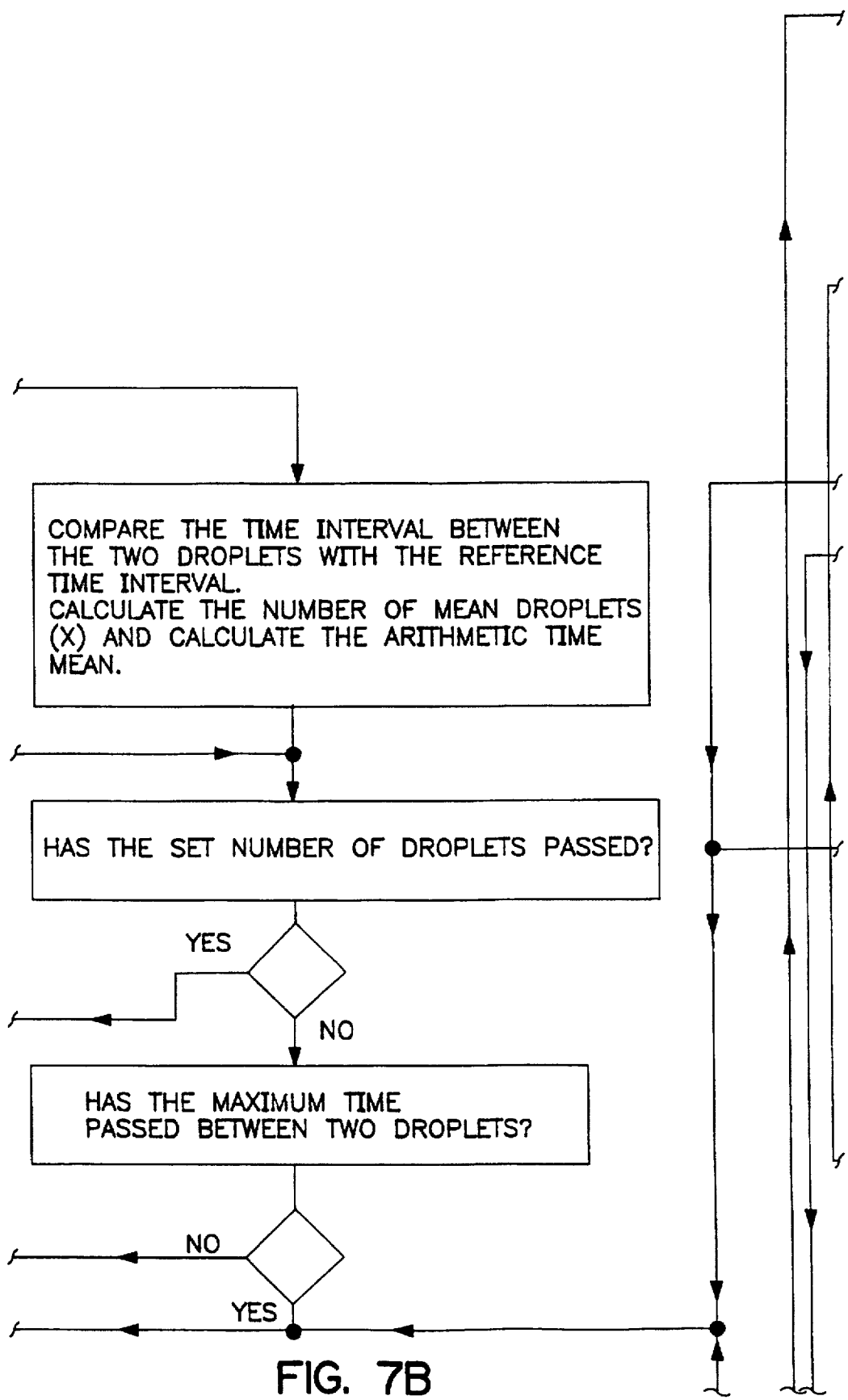
Figure 7C:
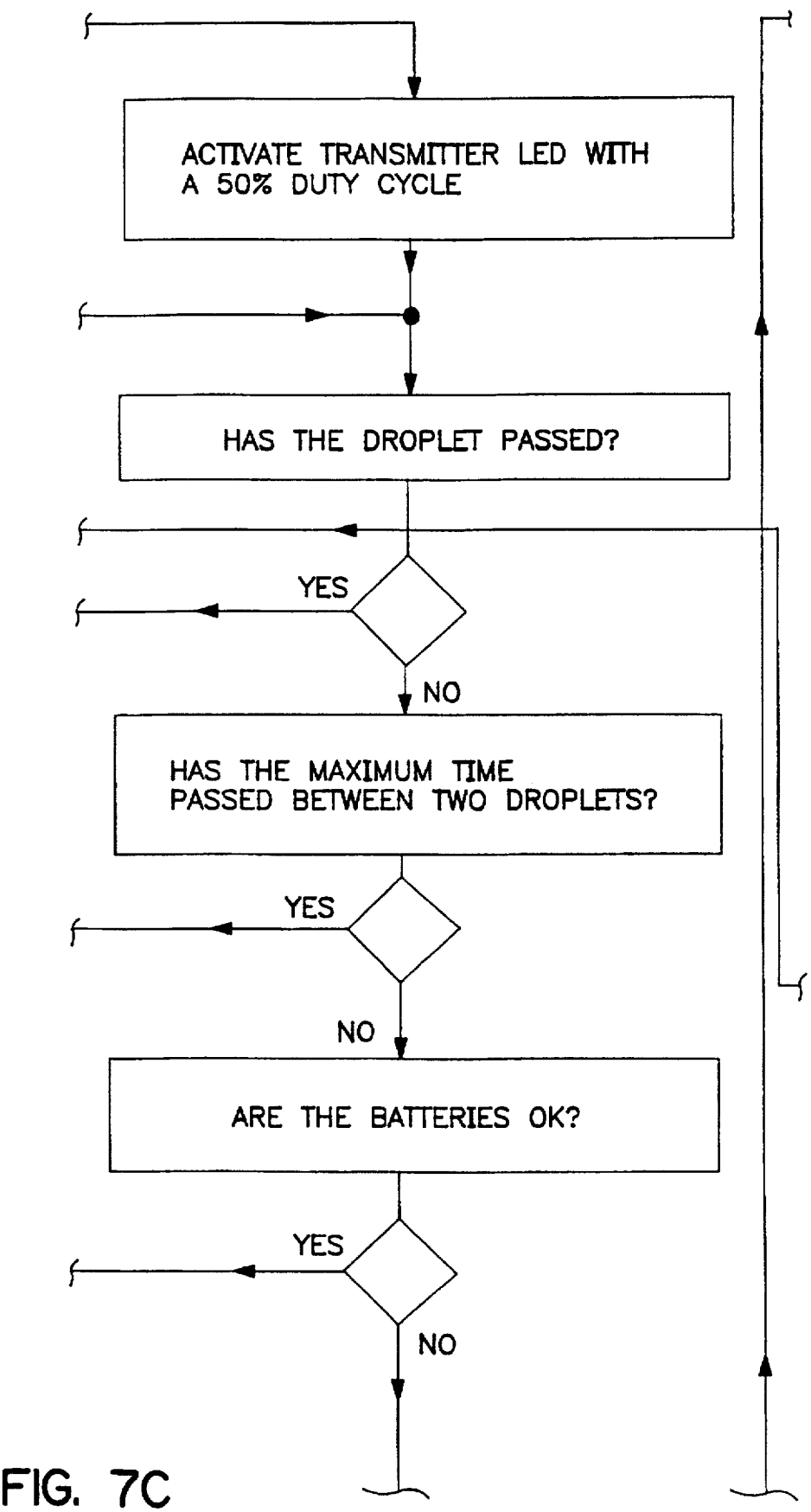
Figure 7D:
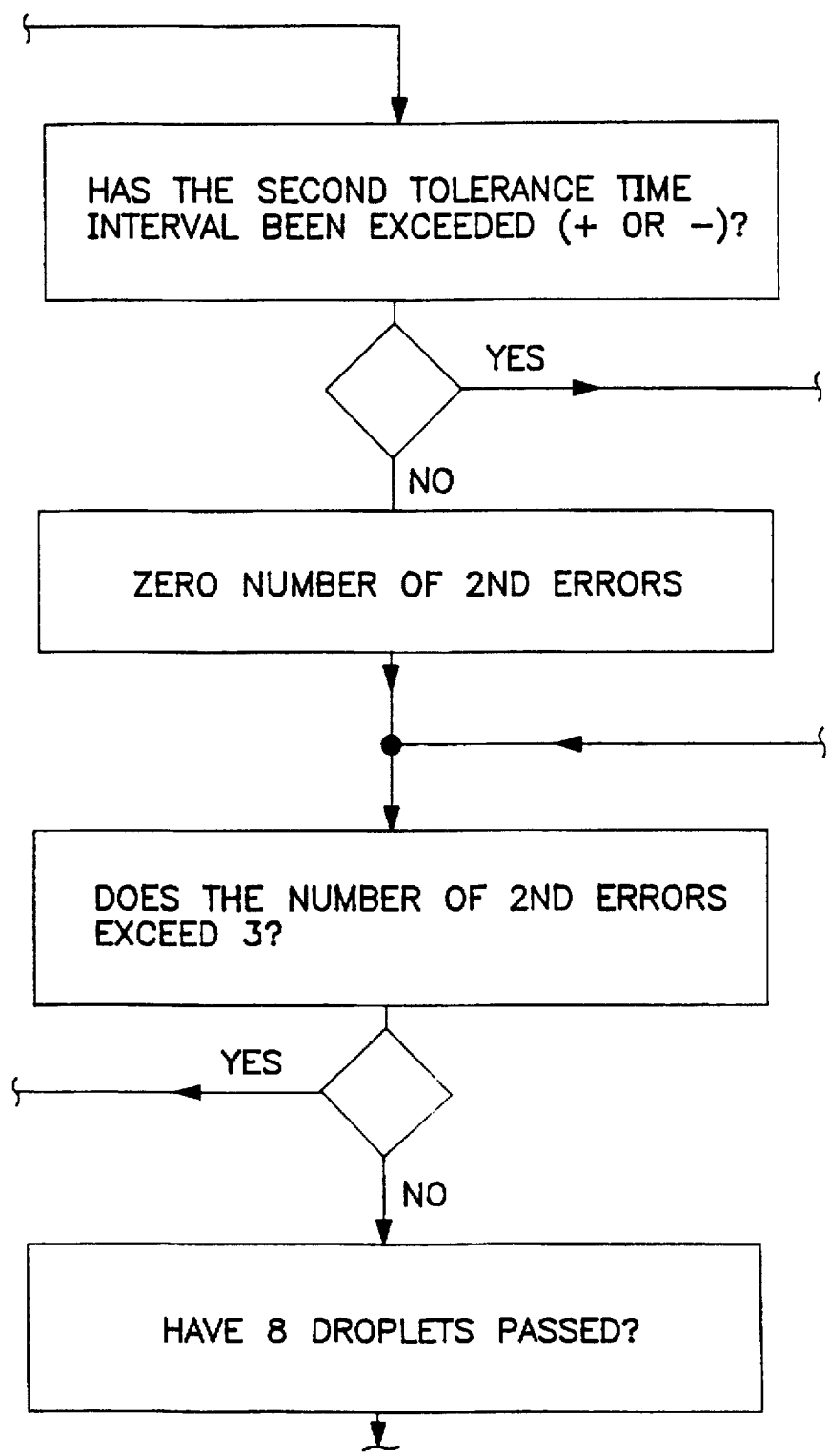
Figure 7E:
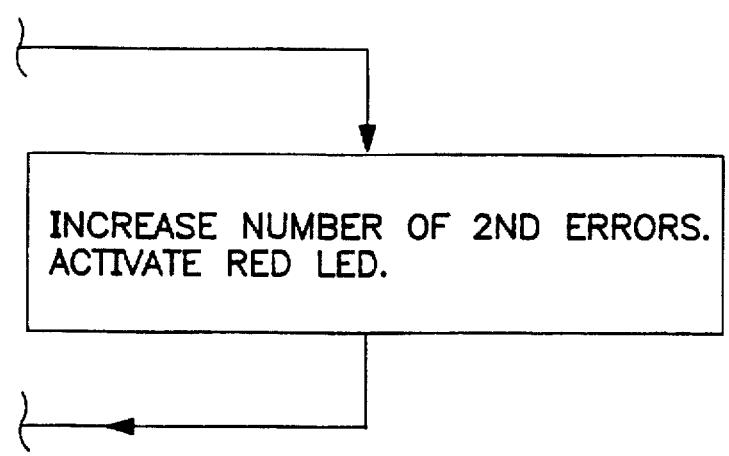
Figure 7F:
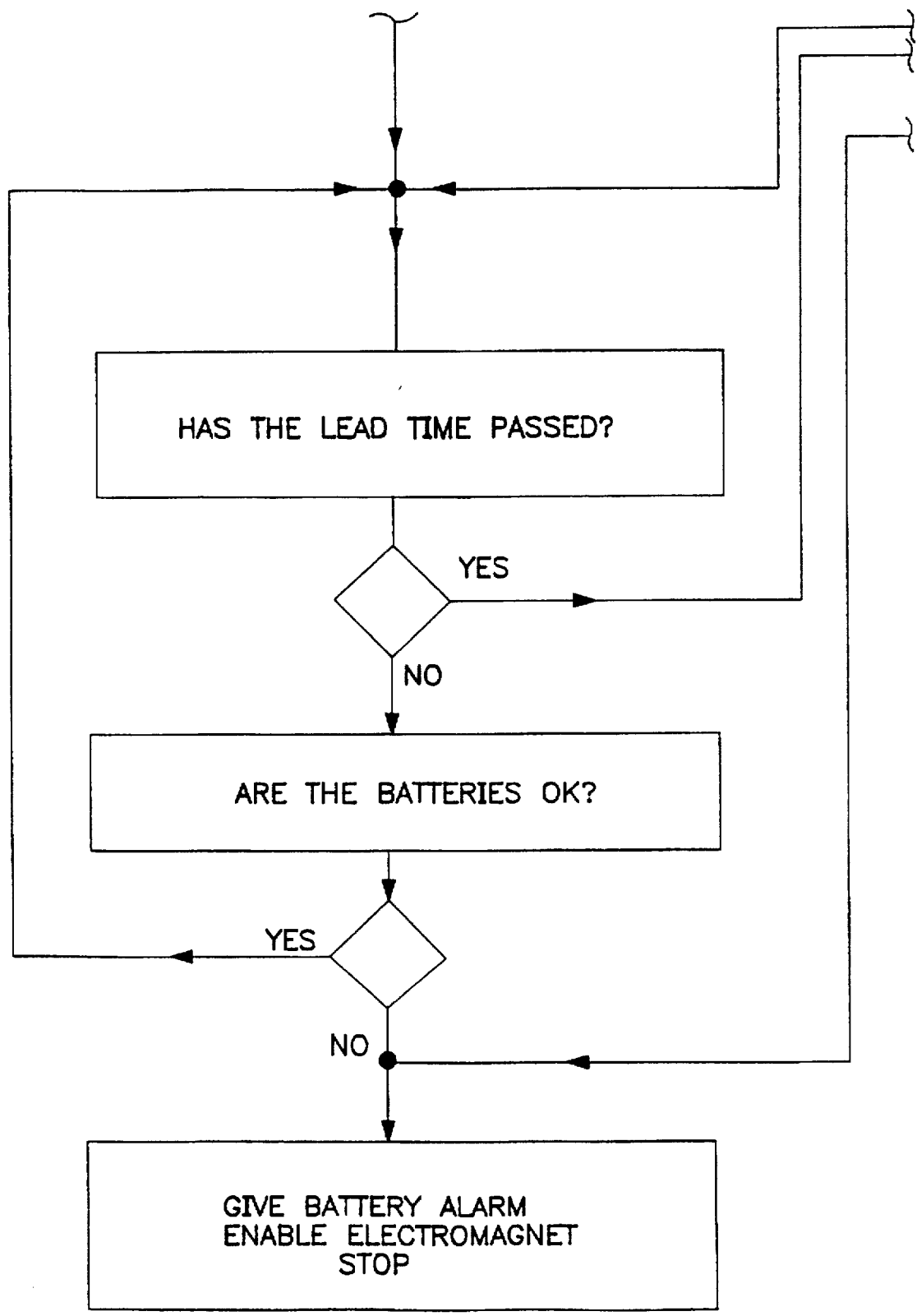
Figure 7G:
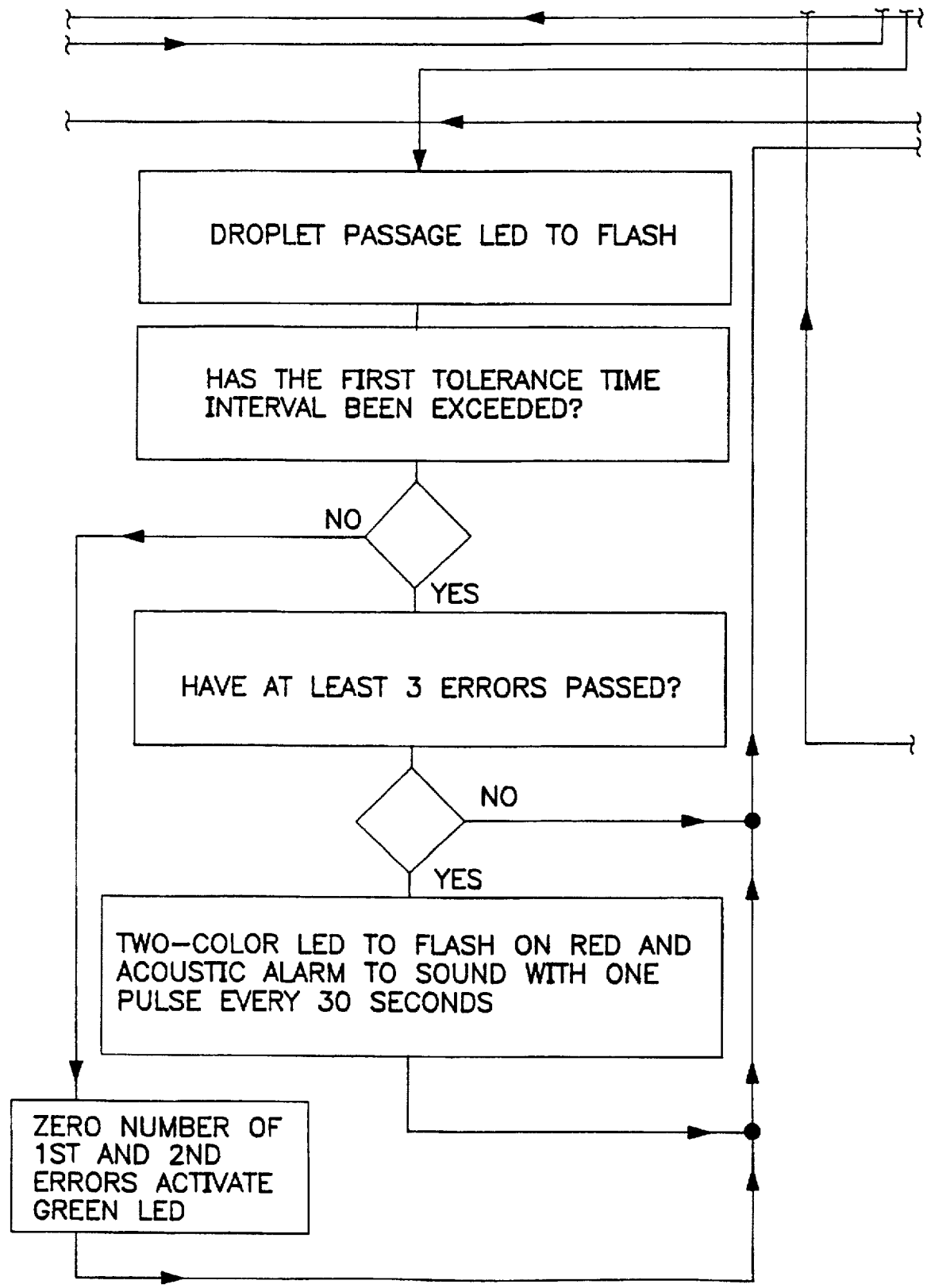
Figure 7H:
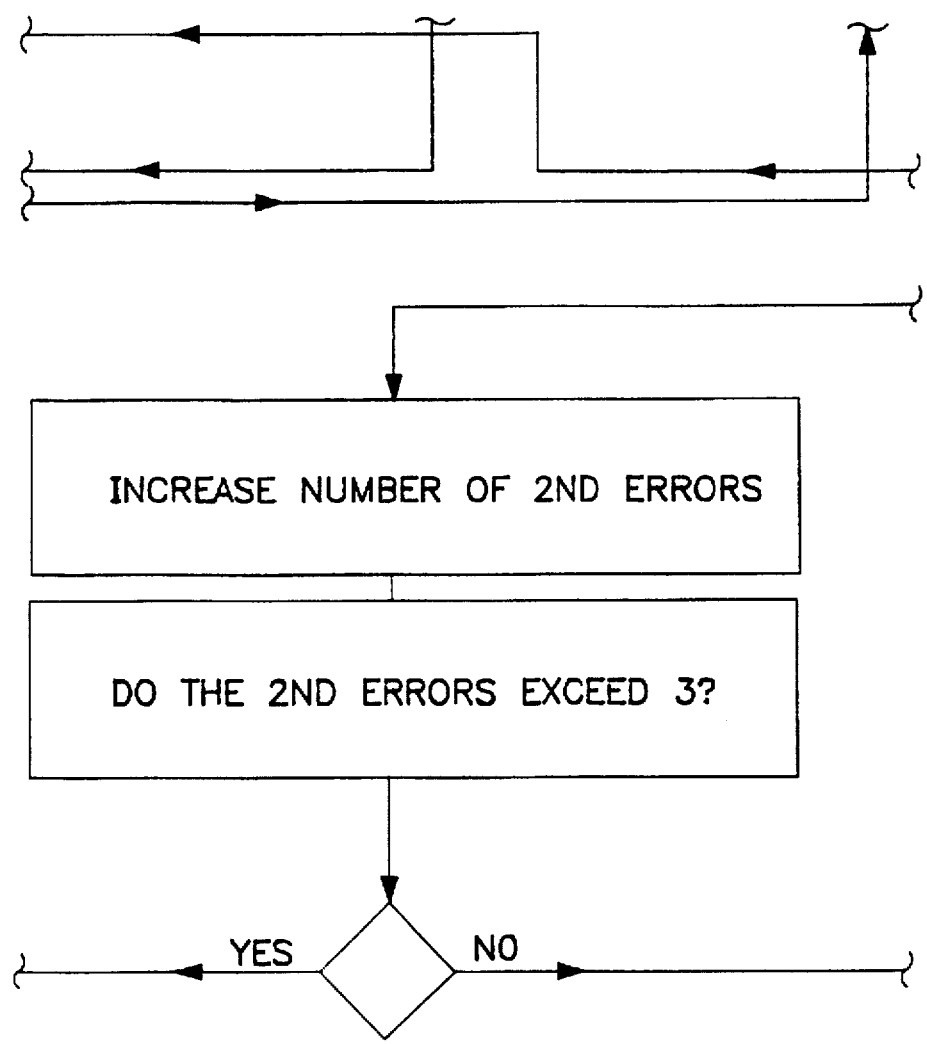
Figure 7I:
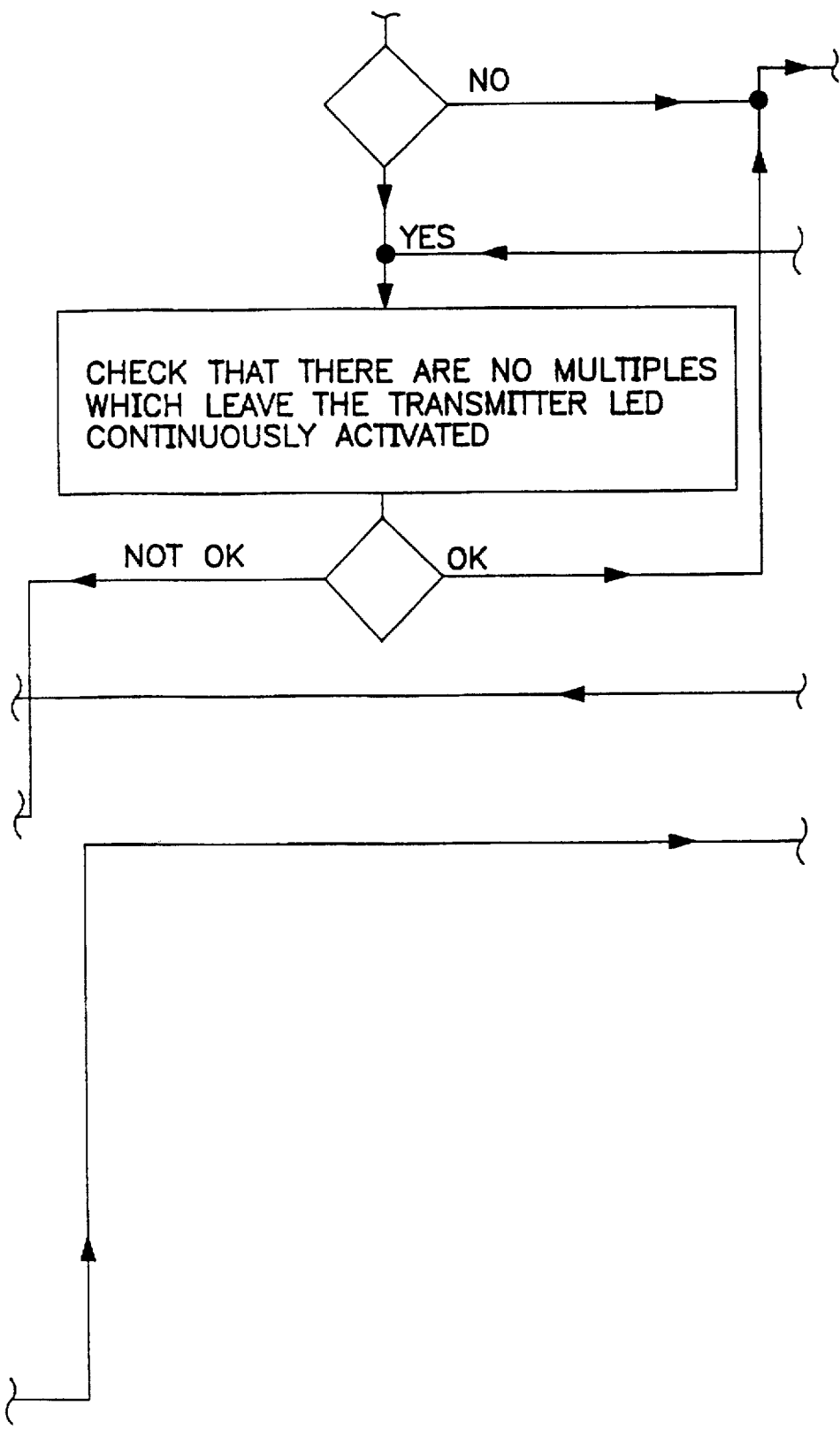
Figure 7J:
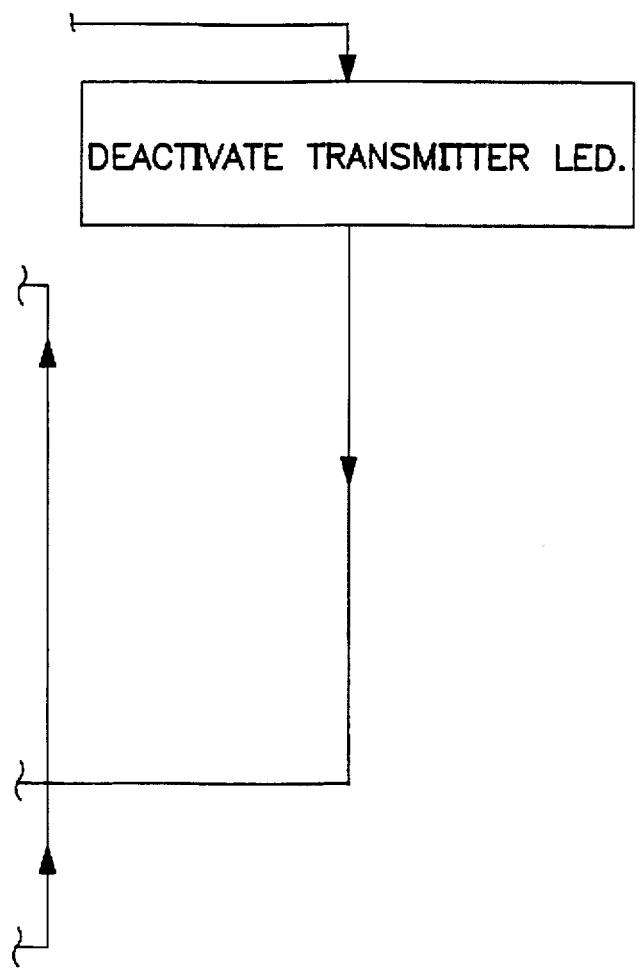
Figure 8A:
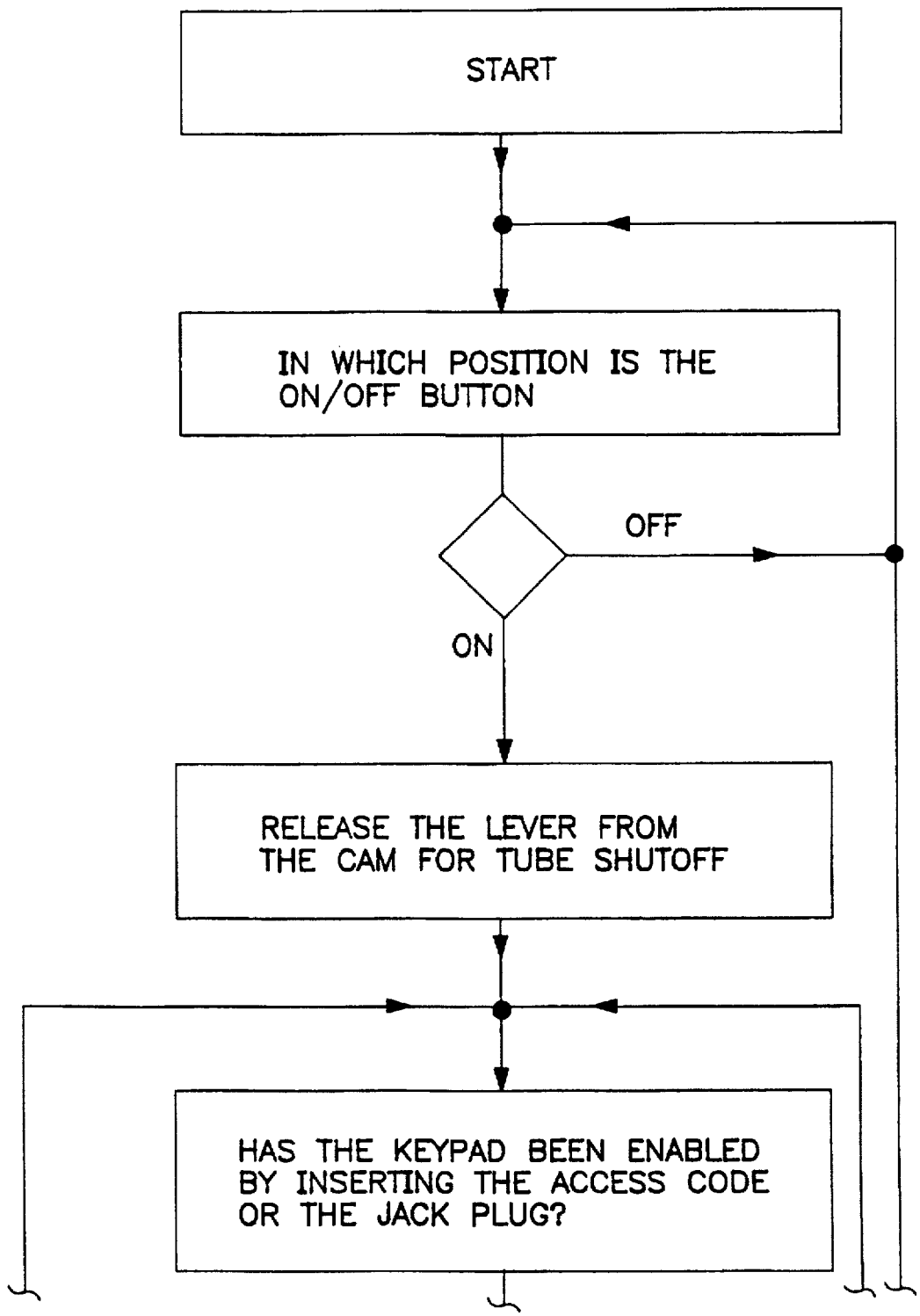
FIG. 8 is a schematic flow diagram corresponding to the operation of a second embodiment of the device electronic circuit of the present invention.
Figure 8B:
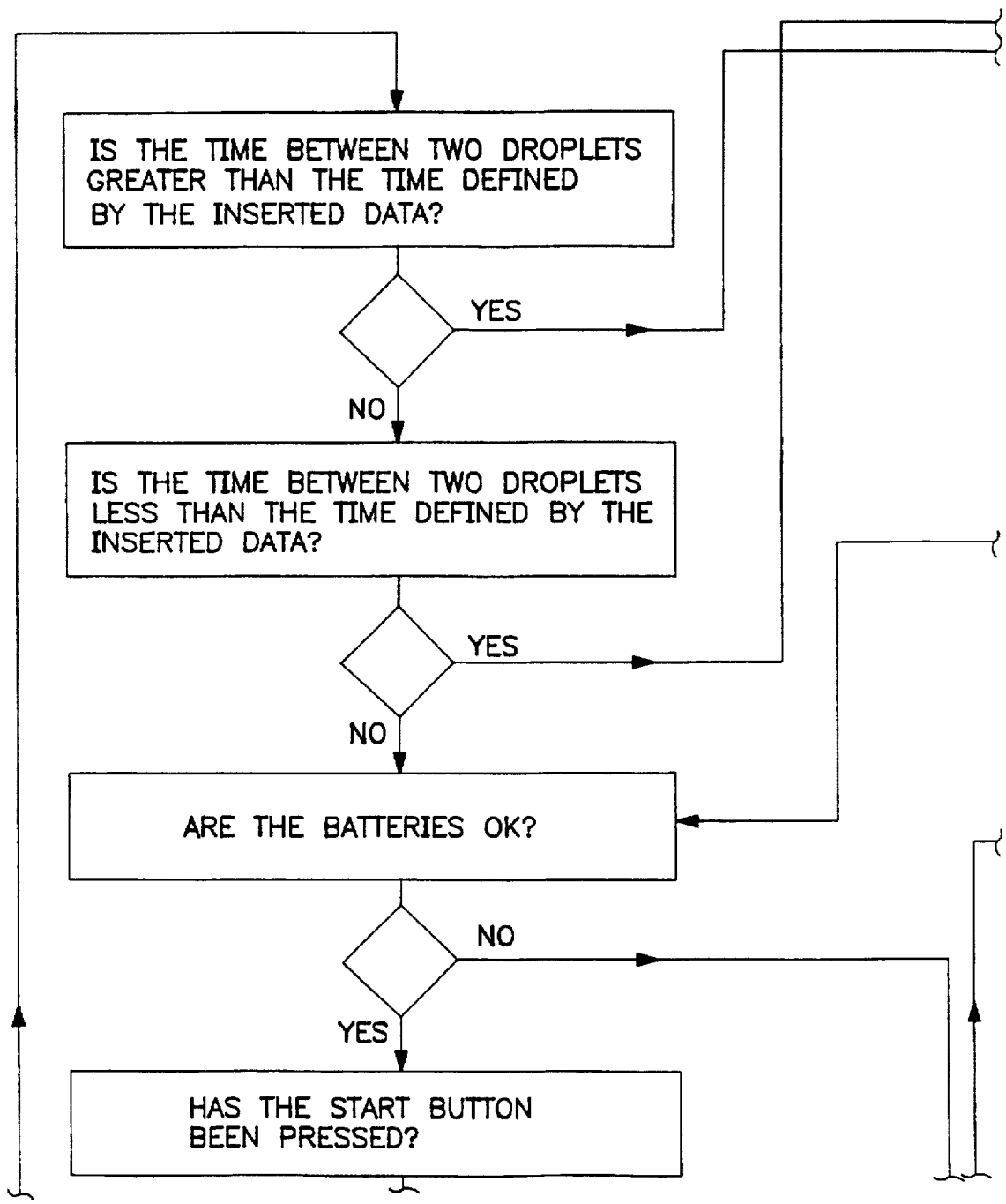
Figure 8C:
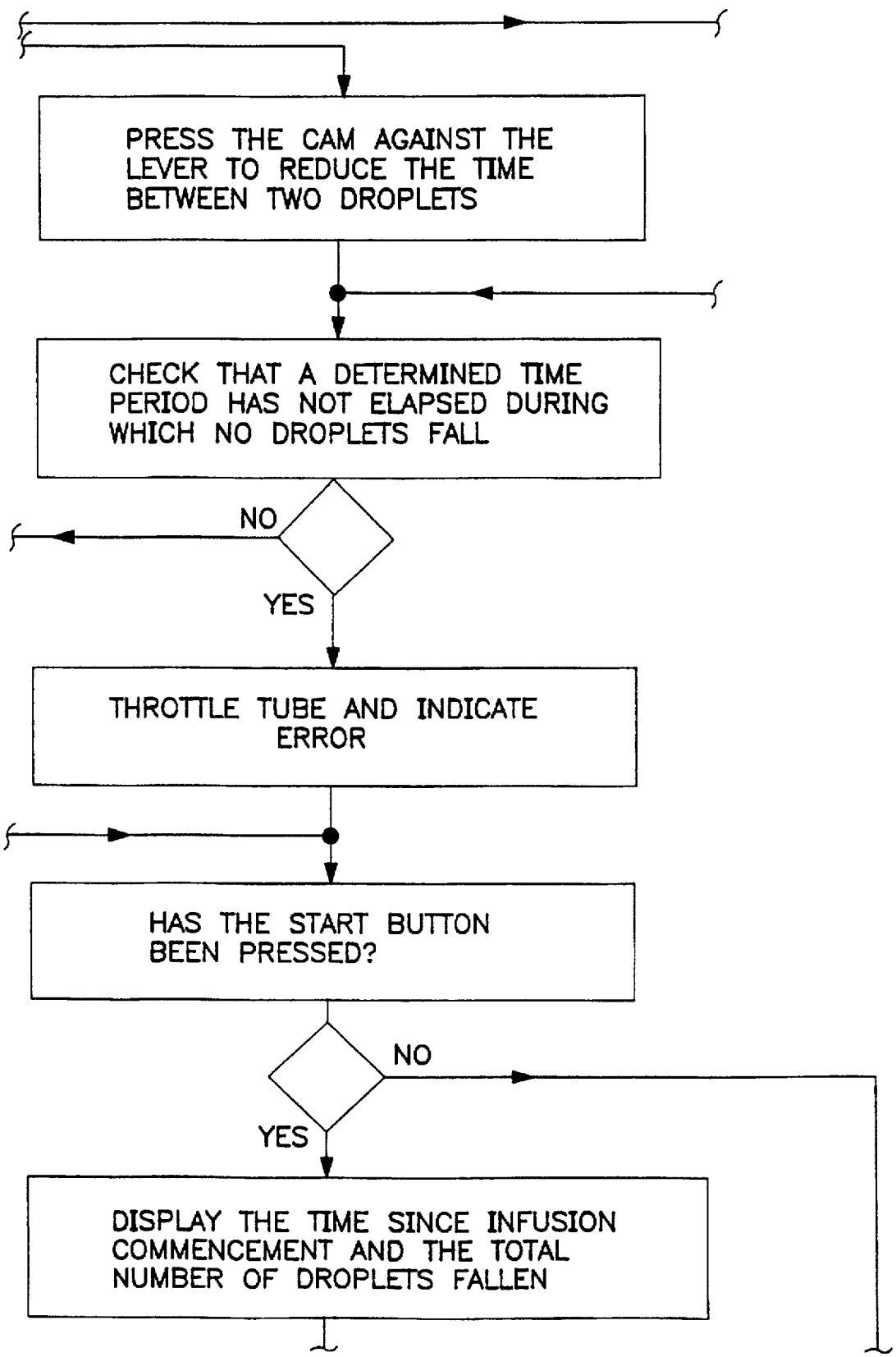
Figure 8D:
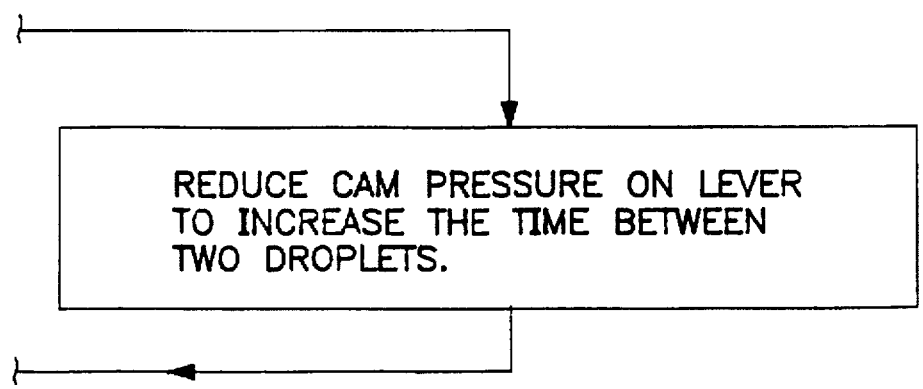
Figure 8E:
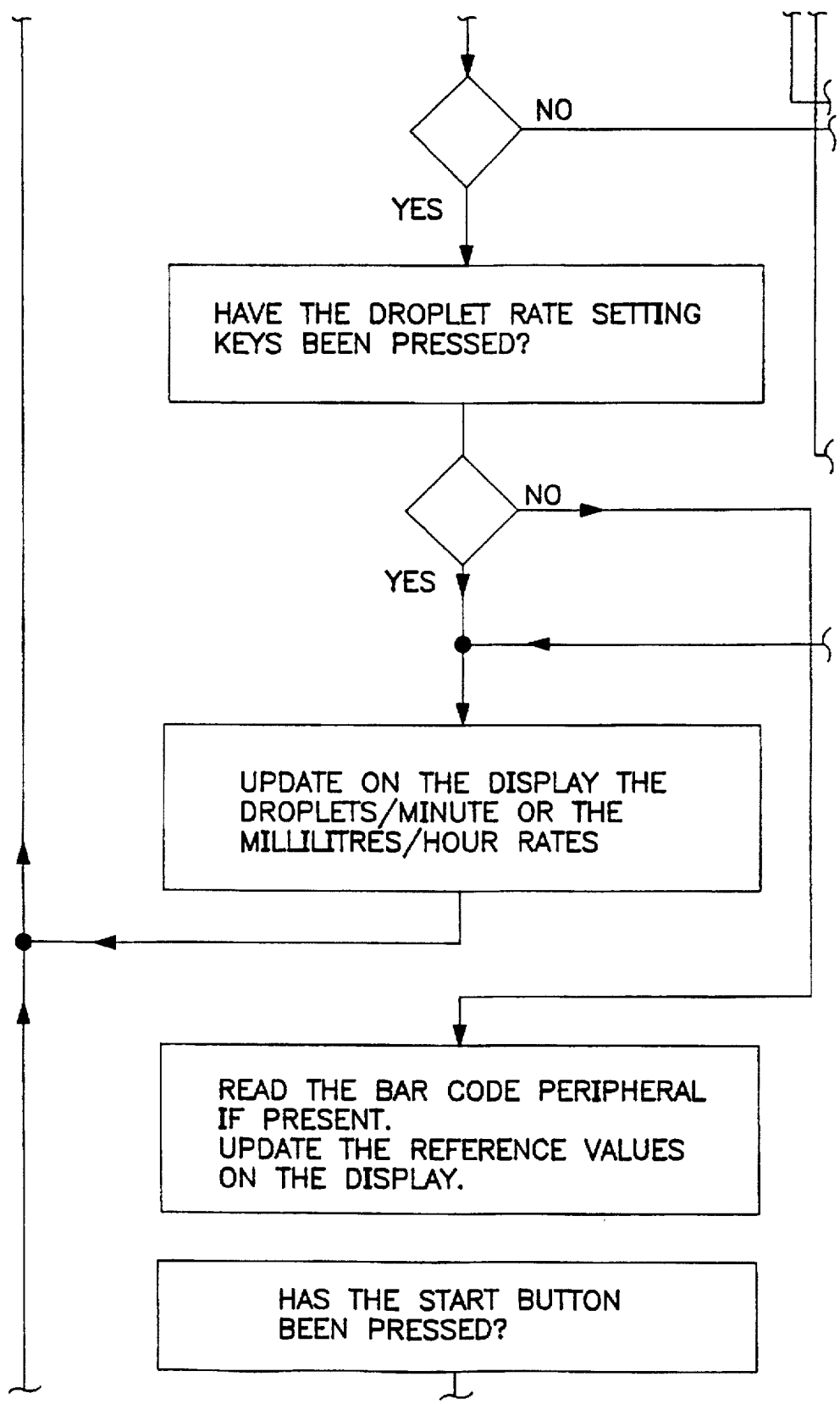
Figure 8F:
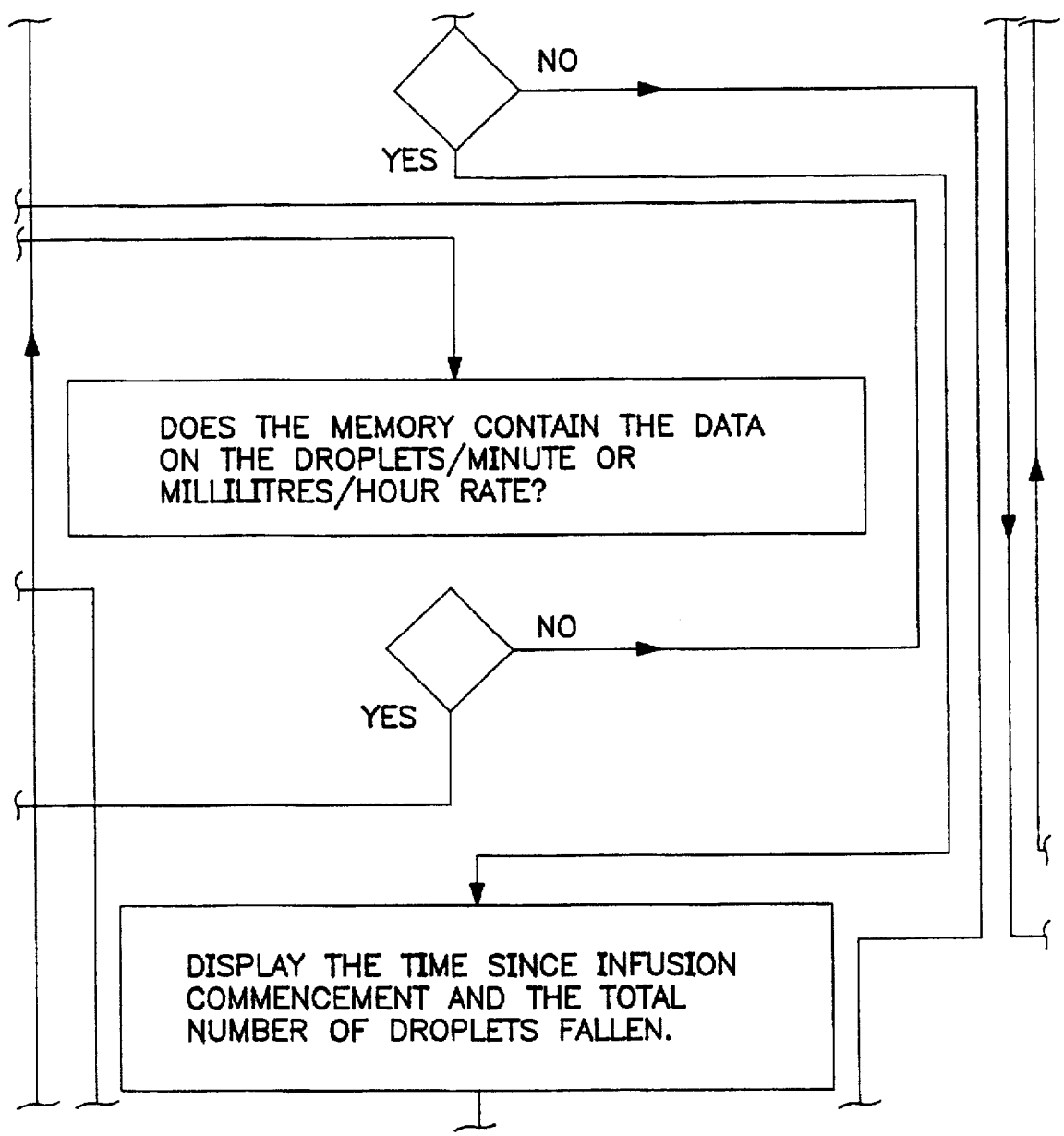
Figure 8G:
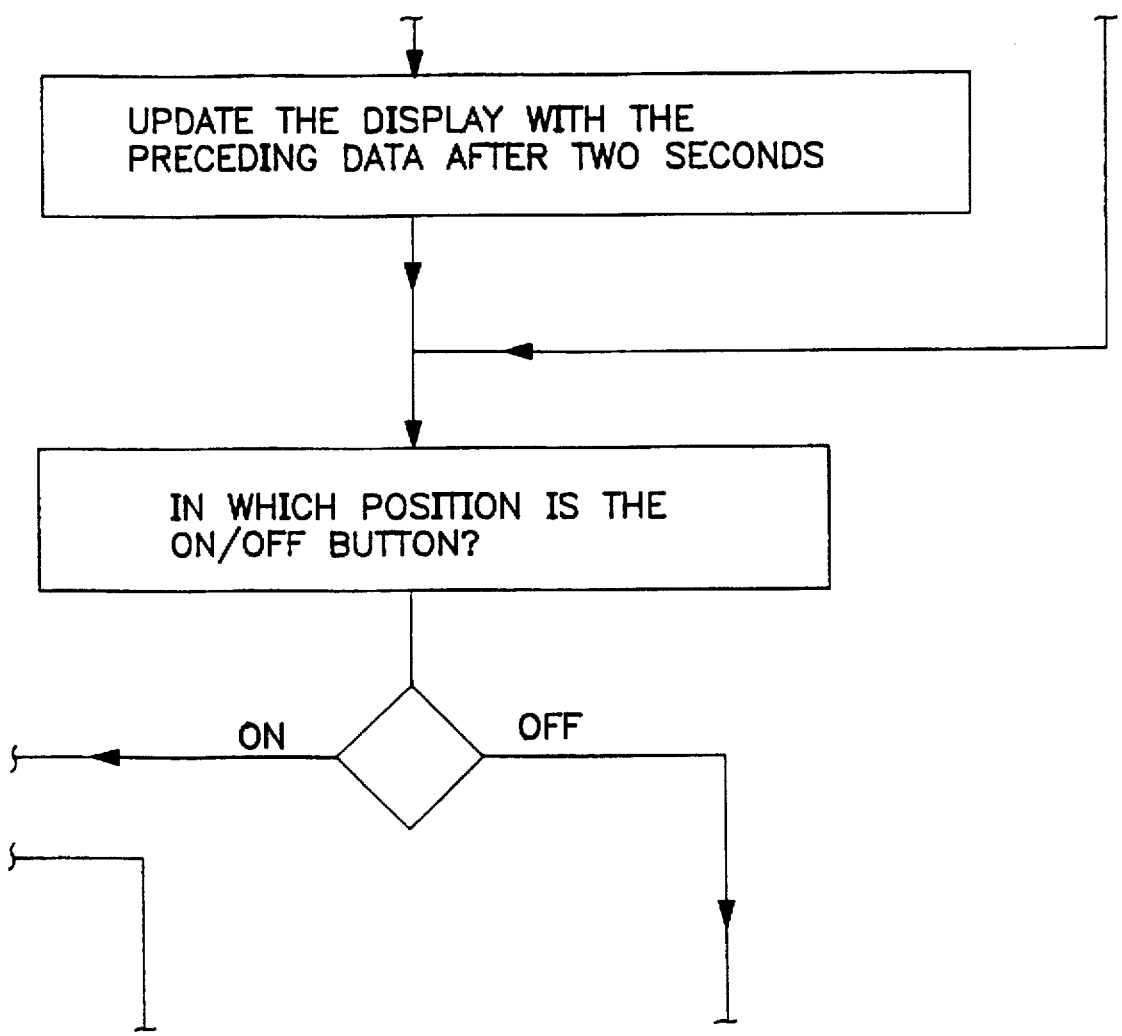
Figure 8H:
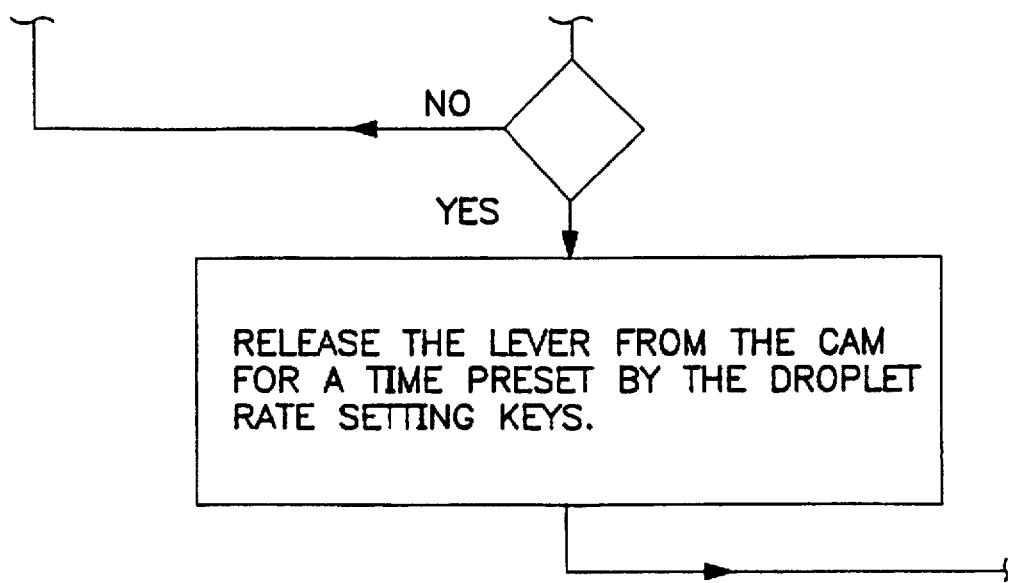
Figure 8I:
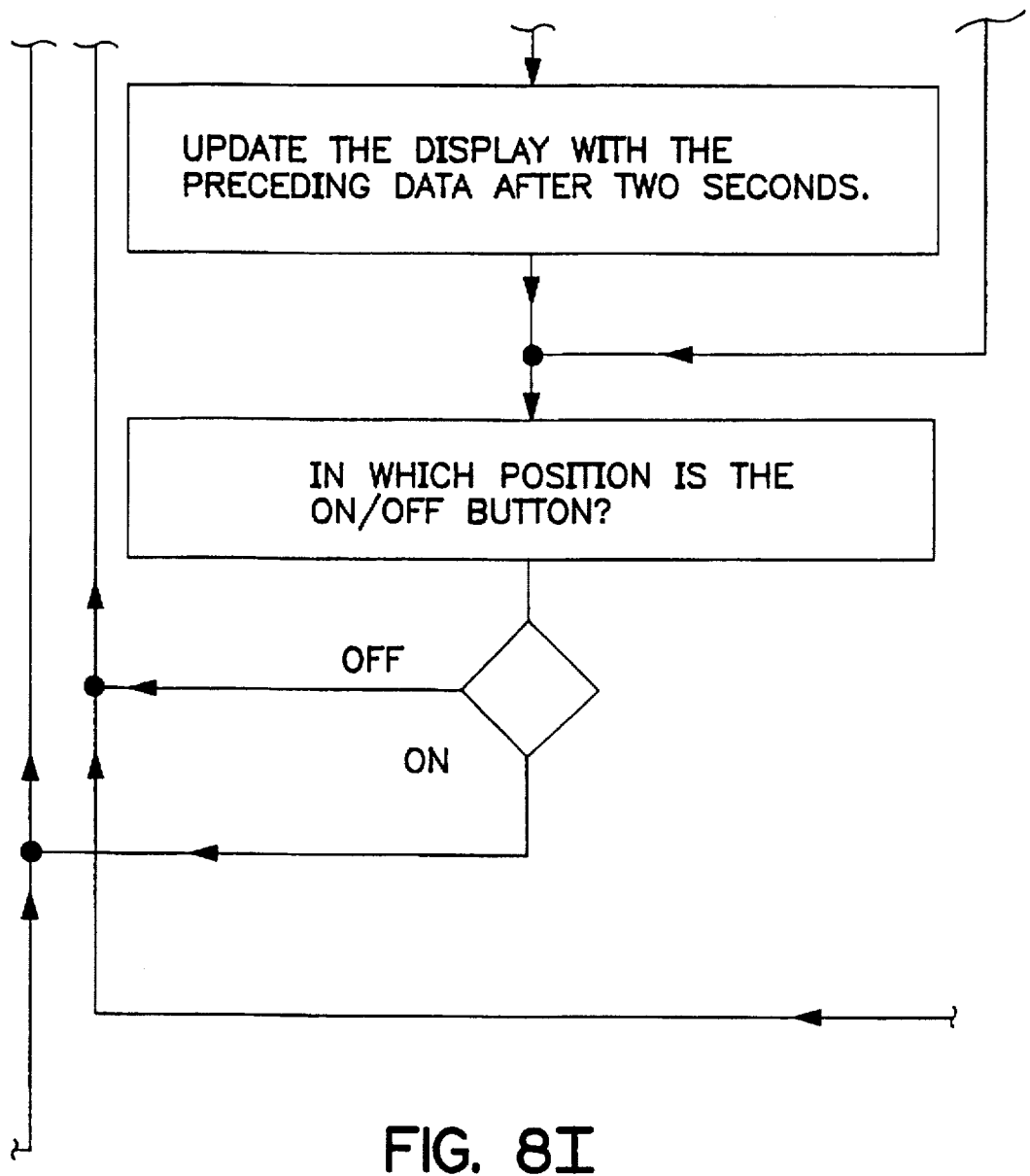
Figure 8J:
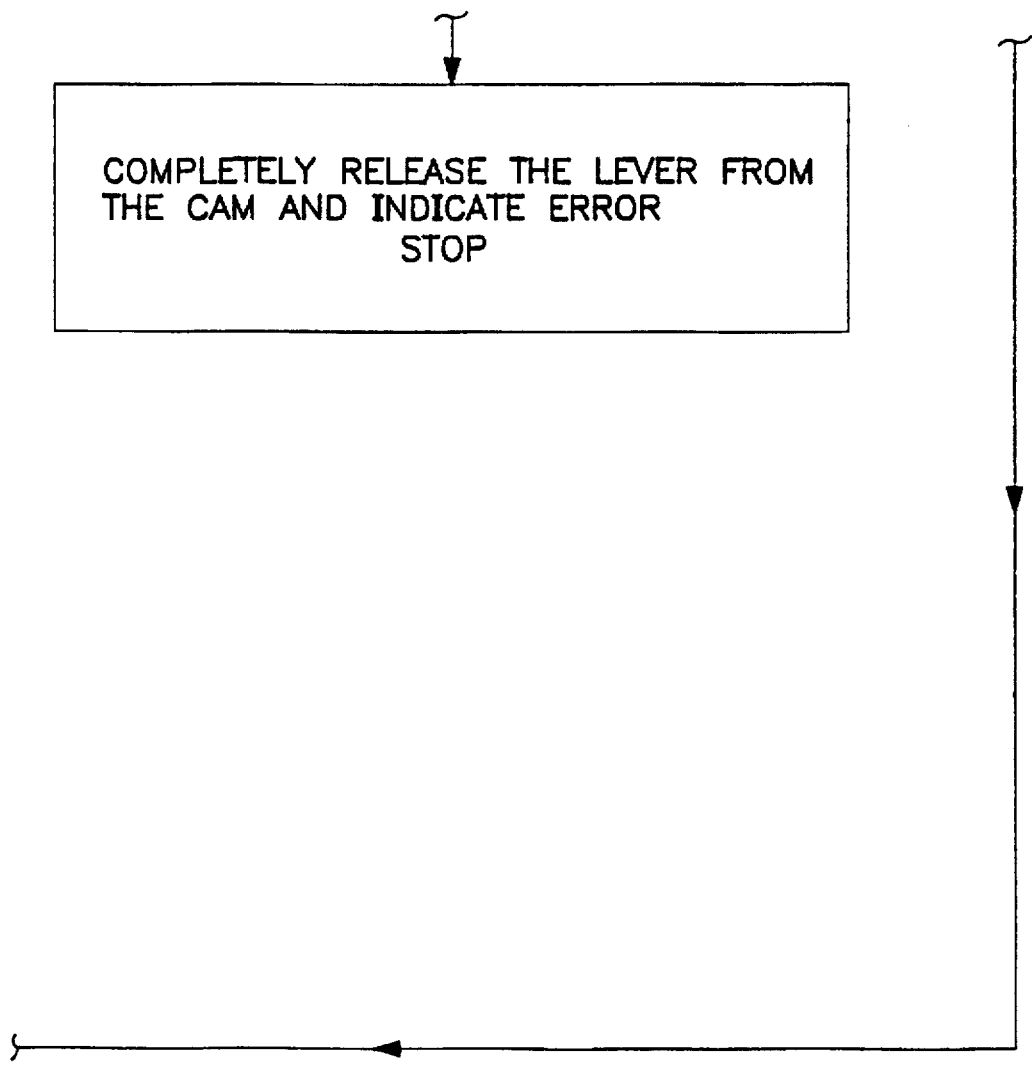

It should be noted that the force exerted by the permanent magnet 27 on the rod 25 is a maximum at the end of its return stroke, ie when said rod 25 has retracted into the electromagnet 5 (FIGS. 3 and 5).

Consequently said force is a minimum when the rod 25 is in the opposite position (FIG. 2), i.e. precisely when it is required to exert maximum force against the end 36 of the trip lever 6. The use of the permanent magnet 27 instead of a spring is therefore particularly advantageous because a spring would exert a reverse action. In practice the force exerted by such hypothetical spring would be a maximum when the rod 25 is positioned at the end 36 of the trip lever 6, and a minimum when the rod 25 has retracted into the electromagnet 5. This is exactly the opposite to that which is required.

In addition, the rod 25 undergoes an "idle stroke" portion before striking the lever 6. The term "idle stroke" means that travel portion through which the rod 25 moves without encountering mechanical resistance. This enables a "hammer effect" to be achieved, making the action of the electromagnet 5 even more effective for equal energy consumption, so making the tripping of the device 1 and consequent shutoff of the administered solution flow more reliable.

The overall operation of the device 1 according to the invention is as follows: after starting and adjusting the intravenous infusion system, the reset pushbutton 26 is pressed to rehook the shutoff device 4 (FIG. 3). At the same time the device is mounted as high as possible about the drip chamber 17 such that the end 32 of the arm 19 of the lever 7 rests completely against the tube 14 of the system.

On activating the device 1, which is done by operating the switch knob 41, the two-colour LED 13 begins to flash rapidly with green light. During this stage the electronic circuit 12 of the device 1 recognizes and memorizes the time intervals between the passage of two consecutive droplets, by means of the infrared emitter diode 28 and the receiver photodiode 29.

This type of automatic self-calibration is achieved by measuring the time interval between the first two solution droplets falling through the drip chamber 17, and comparing this with a reference time interval previously set in the microcontroller 40 to immediately establish, on the basis of this parameter, whether this is a slow infusion or an infusion which can be considered fast.

A determined maximum time period during which the first two solution droplets must fall is fixed. If this maximum time period passes without the sensor detecting the passage of two consecutive droplets, the shutoff device 4 is enabled and measurements are interrupted.

Otherwise, the device establishes the reference infusion time interval by calculating the arithmetic mean of the times involved in a number "x" of time intervals employed in delivering a number "x+1" of successive droplets in the case of slow infusion, and between a number "2x" of time intervals employed in delivering a number "2x+1" of successive droplets in the case of fast infusion. The value "x" is memorized in the microcontroller 40 when this is programmed.

After a few seconds, the flashing of the two-colour LED 13 changes in intensity and follows the frequency with which the droplets fall, a pulse of green light being displayed for each droplet. Having determined the number of time intervals between droplets which is to be used in calculating the arithmetic mean and taking this mean value as the reference value, the microcontroller 40 establishes the values of two tolerance time intervals (these values to be considered in the algebraic sense) and the value of one time interval used for establishing the activation and deactivation periods of the infrared emitter diode 28 (known as the "lead time").

If for three consecutive times the time interval between the passage of two successive droplets exceeds the value of the first tolerance time interval (or is less than its opposite) (1st error), which is indicatively between 16% and 20% of the mean time interval taken as reference, the microcontroller 40 of the device 1 causes the colour of the two-colour LEd 13 to briefly switch from green to red and causes the piezoelectric buzzer 33 to emit a brief acoustic pulse about every 30 seconds (pre-alarm threshold).

In other words, the pre-alarm condition occurs when the difference between the value of the arithmetic time mean and the value of the time interval between the passage of two successive droplets lies between 16% and 20% of the arithmetic time mean.

To return the entire system to normality, the discharge device of the intravenous infusion system has to be adjusted to again achieve the reference rate or until the two-colour LED 13 again flashes green.

If the first and second tolerance time intervals are both exceeded, the alarm operates, but only after at least three consecutive errors to prevent false alarms due to sporadic exceeding of these limits, caused for example by swinging of the bottle or a sudden large entry of air into the bottle.

When for at least three consecutive times the time interval between the passage of two successive droplets exceeds the value of the second tolerance time interval (or is less than its opposite) (2nd error), which is indicatively between 20% and 25% of the mean time interval taken as reference, or if the solution is depleted or if for any problem within the system the solution begins to discharge as a continuous jet, the device enters its definitive alarm state. The previously set shutoff device 4 operates to throttle the system tube 14, so shutting off the flow of the solution to be administered. In addition, the acoustic alarm of the piezoelectric buzzer 33 operates continuously and the two-colour LED 13 operates with rapid red flashing.

In other words the alarm condition arises when the difference between the value of the arithmetic time mean and the value of the time interval between the passage of two successive droplets is between 20% and 25% of the value of the arithmetic time mean. At this point the device is turned off, the intravenous infusion system closed, the reset button 26 pushed and the bottle of medicament again adjusted or replaced.

A further important characteristic: of the device of the present invention is that the infrared emitter diode 28 is pulse-powered in pulse width modulation with a duty cycle of about 50%, hence functioning with pulsating operation. By this means, the electricity consumption is reduces compared with the known art, in which the emitter diode 28 is operated continuously.

Moreover as the emitter diode 28 operates only during the limited time period during which the droplet is assumed to fall, there is a further reduction in electricity consumption.

The lead time during which the emitter diode 28 remains activated with pulsating operation while waiting for the droplet to fall is determined by subtracting a previously fixed reference value stored in the memory of the microcontroller 40 from the arithmetic mean of the time intervals between the passage of two successive droplets.

In addition, to prevent the rate of droplet fall reaching, as the result of a fault or an error by the nursing personnel or patient, an exact multiple of the initial rate determined during the automatic calibration, the microcontroller 40 causes the infrared emitter diode 28 to operate continuously every eight droplets for a time equal to the time interval corresponding to the passage of at least two droplets, and checks whether the delivery is regular during this time interval.

Again in this specific case the emitter diode 28 operates in pulse width modulation to further economize on electricity consumption. With regard to the operation of the device 1 according to the invention, it should also be noted that the operating cycle and the power circuit are totally controlled by the electronic circuit 12 and in particular by the microcontroller 40.

In this respect, although the device can operate for several hours between charges because of the low electricity consumption, the microcontroller 40 also monitors the state of charge of the set of batteries 2 and provides a visual and acoustic alarm signal if the feed voltage falls below a predetermined safety level, after activating the shutoff device 4.

In this case the set of batteries 2 must be completely recharged by connecting a battery charger of traditional type or a dedicated charger to the socket 35 of the device. The permanent magnet 27 is positioned such that when the device 1 is connected to the appropriate external dedicated battery charger, its magnetic force operates another reed switch connected within the dedicated charger, to close the charging circuit.

The microcontroller 40 also performs numerous other functions. It controls the operation of a time base (free running operation, of about 5 ms) for controlling the activation and deactivation of the emitter diode 28, the two-colour LED 13 and the buzzer 33; it calculates and memorizes the droplet waiting time; when this waiting time has expired it activates a counter while at the same time activating the emitter diode 28; it halts said counter when the expected droplet arrives, while at the same time deactivating the emitter diode 28; it compares the value of the time interval between the passage of two successive droplets read on the counter with the previously calculated tolerance time intervals and handles any errors encountered by operating the two-colour LED 13 on red and operating the buzzer 33 about every 30 seconds in the case of a pre-alarm, or increasing the frequency of operation of the two-colour LED 13 on red and maintaining the buzzer in continuous operation with simultaneous activation of the shutoff device 4 for the system tube 14 in the case of a definitive alarm.

The characteristics of the device for monitoring and controlling an intravenous infusion system according to the present invention are clear from the aforegoing description, as are its advantages. Numerous modifications can be made to the device of the present invention by an expert of the art without leaving the scope of protection of the inventive idea.

For example the piezoelectric buzzer 33 can be replaced by a known voice synthesis apparatus or by a radio or cable connection system to enable the pre-alarm or alarm warning to be transmitted to remote operators or nursing personnel if the device is used in a hospital.

Moreover, if the rate of droplet fall slows down (this usually not constituting a danger but merely an unwelcome prolongation of the infusion), a reversible acoustic alarm could replace the definitive alarm and the tripping of the shutoff device 4. In this respect, it is typically the case that, while sleeping, a patient may bend the arm into which the needle of the intravenous infusion system is inserted, with the result that the droplet fall rate slows down. In this case the acoustic alarm would waken him to the extent required to move the arm and restore the natural delivery of the infusion, causing cessation of the alarm and the return of the patient to sleep.

Figure 9:
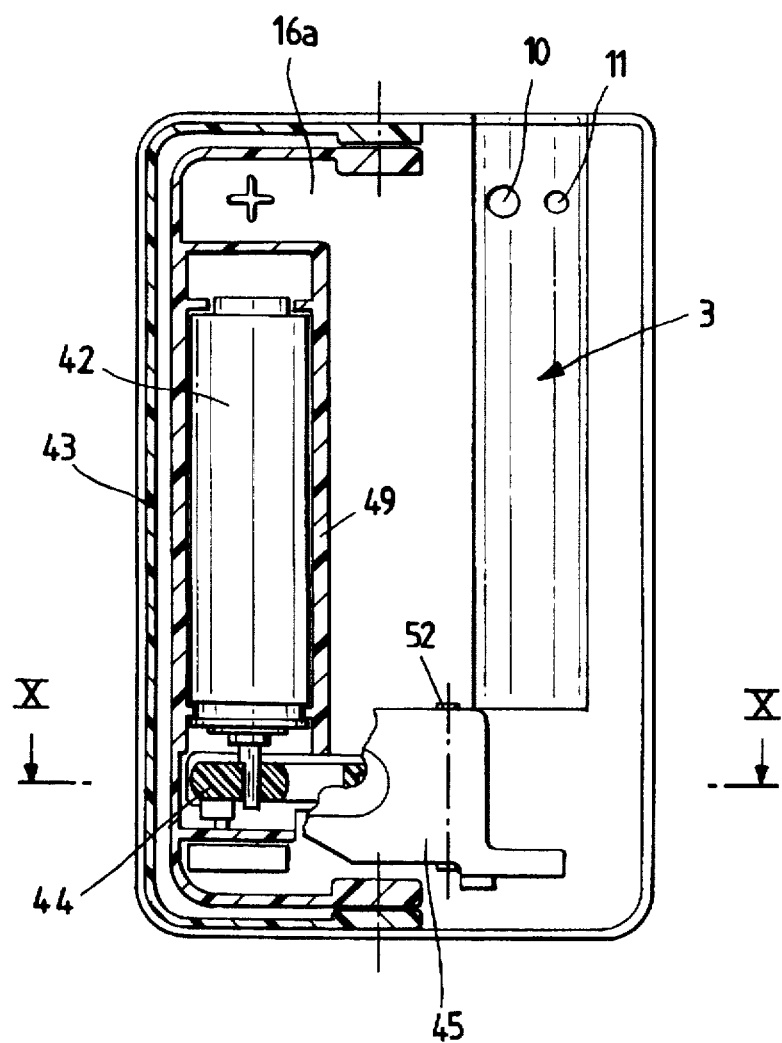
FIG. 9 is a schematic plan view of one of the compartments of the second embodiment of the device according to the present invention.

In a second embodiment of the present invention, the infusion rate can be automatically regulated and maintained constant (while maintaining substantially the same dimensions and same electricity consumption as the first version provided with the shutoff device), by gradual squeezing of the tube 14 of the intravenous infusion system. This is made possible by replacing the trip lever 6, the shutoff lever 7, the springs 8 and 9 and the electromagnet 5 forming the shutoff device 4, by a direct current geared motor 42 (FIG. 9) which acts, via a cam 44, on a lever 45 very similar to the shutoff lever 7 of the preceding embodiment, loaded by a torsion spring 46. The new lever 45 differs from the preceding by being provided with a protuberance 47 on which the cam 44 acts and utilizes the principle of advantageous first class levers, having a fulcrum 52 closer to the point of application of the force which throttles the tube 14 than to the point of application of the force impressed by the contour 51 of a cam 44. Because of the particular structure of the lever 45 and of the relative pertaining parts, the regulator device can be operated by a geared motor 42 of tendentiously small overall size in relation to the required throttling force for the tube 14.

A seat 49 for the geared motor 42 is formed directly by the mould used for producing a compartment 16a, in which the lever 45 is also housed.

Figure 10:
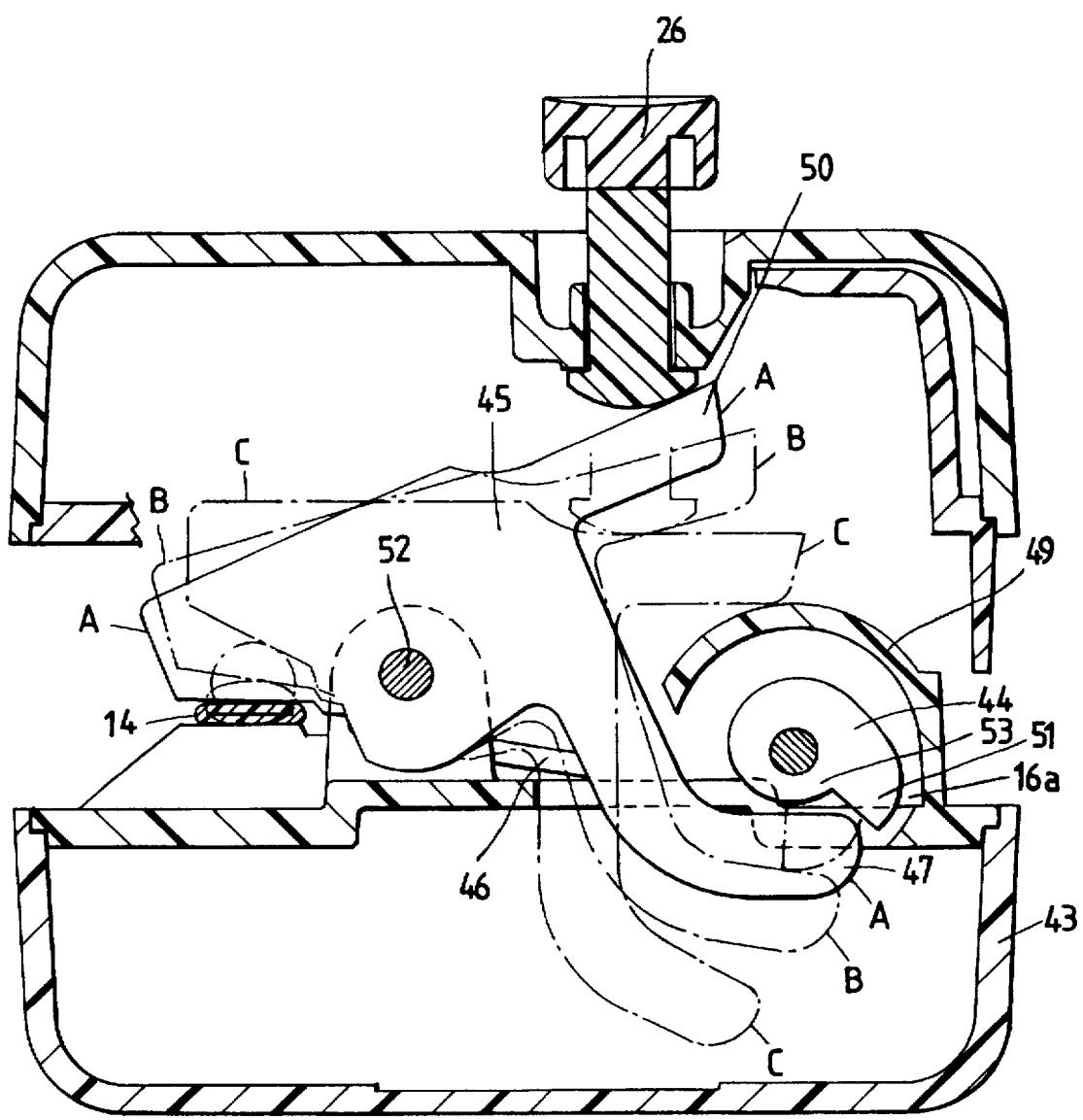
FIG. 10 is a schematic section through the device of FIG. 9, taken on the line X—X.

To further increase sensitivity, the entire travel of the cam 44 can be used exclusively for regulating the tube 14, from totally closed (lever 45 completely freed from the cam 44) to maximum allowable tube opening (lever 45 totally pressed by the cam 44). With reference to FIG. 10, A and B indicate in succession the extreme positions which the lever 45 assumes during operation of the geared motor 42 and rotation of the cam 44, from the tube 14 totally closed (position indicated by A, shown in full lines) to the tube 14 partially open (position indicated by B, shown in dashed and dotted lines).

During its operation, the geared motor 42 transmits rotary motion to the cam 44, the extent of opening of the tube 14 being regulated by the lever 45, which continuously assumes all positions between that indicated by A (tube 14 throttled), with a minor diameter part 53 of the cam 44 facing but not resting on the protuberance 47, and that indicated by B (maximum allowable opening of the tube 14 during operation of the geared motor 42), with the contour 51 of the cam 44 engaged with the protuberance 47, to completely press the lever 45.

To release the tube 14 and separate the device 1 from the drip chamber 17, the reset button 26 has to be pushed. On doing this, the lever 45 assumes the position indicated by C, shown in dashed and dotted lines. The protuberance 47 is completely disengaged from the cam 44, and the end 50 lies on the abutment surface 49 of the geared motor 42.

Using this structure and employing only the force of gravity to which the droplet passing through the drip chamber 17 is subjected, and of which the rate is regulated by the degree of squeezing of the tube 14 by the lever 45, the movement undergone by the liquid can result in constant and controlled infusion. If adjuvant medicaments (nutrient or rehydrating solutions) are to be administered to the patient between one treatment and the next, such administration can be done in the patient's home so as not to waste hospital bed space, and at the same time leave the patient in his own family environment. However the patient cannot then always be supervised by specialist personnel, so making it difficult to ensure correct and constant infusion.

This further embodiment can be used to obviate this drawback, hence avoiding the use of large infusion pumps of relatively high cost and energy consumption, or the use of motor and cam systems of the known art which act directly on the tube of the system and hence require a relatively high transmitted torque. The solution flow control functions are performed by elements housed in one of the compartments forming the structure of the container of the intravenous infusion apparatus, and have low electricity consumption.

The data regarding the infusion rate can be set by a keypad (not shown) provided on the outside of the container of the device 1 and having four keys: one for device activation and deactivation, two for setting the desired number of droplets per minute (one for increasing the number and the other for decreasing it) and the fourth for starting.

The data inserted via the keypad are converted into digital signals and then transformed into electrical signals which control the operation of the geared motor 42.

Said data can also be obtained from a label applied to the bottle by medical personnel and carrying a bar code indicating the particular infusion rate for that type of medicament and personalized for each patient, to be read by a laser diode reader (not shown) installed on the body of the device 1, for display on a liquid crystal display (not shown), which alternately displays the set rate of infusion (in droplets per minute or millilitres per hour), the actual rate of infusion, the time which has passed since infusion commenced and the total number of droplets which have fallen, plus an indication of whether a droplet is falling, whether the battery charge is low, whether the motor is closing or opening, and of the data fed in via the keypad or via the bar code.

On termination of infusion, the average droplet volume can be established by reading on the display the number of droplets used to infuse the volume of medicament contained in the bottle. This information can be used in a subsequent infusion by feeding it in via the keypad or bar code to allow the relationship between droplets per minute and millilitres per hour to be calculated so that the device can convert droplets per minute to millilitres per hour (or to other units of measurement, depending on the country in which it is used).

If home infusions are to be all identical and repetitive, the data can alternatively be fed in via the keypad by the responsible hospital personnel, using either an access code or a jack plug (not shown), the absence of which prevents use of the keypad. When the patient switches on the apparatus in his own home, this system automatically regulates the infusion in accordance with the preset data, which cannot be changed without the use of the appropriate access code or plug.

In this manner the patient is freed from the need to regulate, and possible errors and/or tampering are prevented. In this case the electronic circuit 12 would contain a memory capable of storing the data preset in hospital by the appropriate personnel.

Numerous other modifications can also be made to the monitoring and control device of the present invention without departing from the scope of protection provided by the inventive idea, and in addition in the practical implementation of the invention the illustrated details can be different in form or be replaced by technically equivalent elements.

I claim:

1. A device for monitoring and controlling an intravenous infusion system (1) comprising:

at least one electrical storage battery (2);

a housing (3) adapted to be closed about a drip chamber (17) from which a tube (14) of intravenous infusion system emerges;

a shutoff device (4) having an electromagnet (5) and being constructed and arranged to trip respective first and second levers (6, 7) biased by respective first and second springs (9, 8); and electronic circuit means (12) comprising control means contained within microcontroller means (40), sensor means (28, 29) for sensing droplets, generating droplet signals and transferring droplet signals to the microcontroller means (40) for either activating or not activating indicating means (13, 33);

said electronic circuit means (12) further includes:

means for activating the sensor means (28, 29), means for measuring the time interval between the passage of two consecutive droplets;

means for comparing the value of said time interval with a first reference time interval originally preset in the microcontroller means (40), to recognize whether the infusion underway is of the type classifiable as slow or fast; means for calculating the arithmetic mean of the times elapsing between a number of successive droplets, the number of successive droplets being preset originally in the microcontroller means (40) on the basis of the type of infusion, such that for fast infusion this number is greater than the corresponding number preset for slow infusion;

said comparing means further compares said arithmetic time mean with the time interval between two successively delivered droplets to establish whether said time interval between two successively delivered droplets is equal to the value of the arithmetic mean plus or minus a first or second tolerance time interval originally preset in the microcontroller means (40);

means for setting one of a pre-alarm condition and an alarm condition depending on the extent of the difference between the value of the arithmetic time mean and the value of the time interval between the passage of two successive droplets;

means for activating the indicating means (13, 33) both when in the pre-alarm condition and when in the alarm condition;

means for activating the shutoff device (4) only when in the alarm condition; and means for interrupting the operation of the sensor means (28, 29) during a second time interval included within the time interval between the passage of two successive droplets.

2. A device as claimed in claim 1, wherein the pre-alarm condition arises when, for at least three consecutive times, the difference between the value of the arithmetic time mean and the value of the time interval between the passage of two successive droplets is between 16% and 20% of the value of the arithmetic time mean.

3. A device as claimed in claim 1, wherein the alarm condition arises when, for at least three consecutive times, the difference between the value of the arithmetic time mean and the value of the time interval between the passage of two successive droplets exceeds 20% of the value of the arithmetic time mean, said alarm condition also arising in the case of delivery interruption.

4. A device as claimed in claim 1, wherein said sensor means (28, 29) are powered pulse-wise intermittently.

5. A device as claimed in claim 1, wherein said sensor means (28, 29) operate pulse-wise discontinuously, but uninterruptedly during the time interval between the passage of at least two successive droplets.

6. A device as claimed in claim 5, wherein said sensor means (28, 29) operate uninterruptedly after the delivery of groups of eight successive droplets.

7. A device as claimed in claim 1, wherein the time interval during which the operation of the sensor means (28, 29) is interrupted is determined on the basis of the following algorithm: the value of the arithmetic mean of the times elapsing between a number of successive droplets less a value preset in the microcontroller (40).

8. A device as claimed in claim 7, wherein said microcontroller means (40) comprises an element (24) arranged to count said time interval and/or the activation times and/or the deactivation times of the indicating means (13, 33).

9. A device as claimed in claim 7, wherein said microcontroller means (40) continuously monitors the state of charge of said set of electrical storage batteries (2) and activates said indicating means (13, 33) when said state of charge falls below a level preset in the microcontroller (40).

10. A device as claimed in claim 1, wherein said sensor means (28, 29) are of an optical type.

11. A device as claimed in claim 10, wherein said sensor means (28, 29) are an emitter diode and a photodiode operating within the infrared spectrum.

12. A device as claimed in claim 1, wherein said sensor means (28, 29) include at least one transmitter element (28); at least one receiver element (29) positioned on the same side as and adjacent to the transmitter element (28), with respect to a vertical axis which constitutes the trajectory undertaken by a droplet within the drip chamber (17); and at least one reflector means (30) situated opposite to said receiver and transmitter elements (29, 28, respectively).

13. A device as claimed in claim 12, wherein said reflector means (30) is a concave mirror.

14. A device as claimed in claim 13, wherein said reflector means (30) is located on a base of a cavity (31).

15. A device as claimed in claim 1, wherein said indicating means (13, 33) are of optical and/or acoustic type.

16. A device as claimed in claim 15 wherein said indicating means of optical type are at least one two-colour LED (13).

17. A device as claimed in claim 16, wherein said two-colour LED (13) assumes one of the two colours when in the pre-alarm condition.

18. A device as claimed in claim 16, wherein said two-colour LED (13) assumes the other colour when in the alarm condition.

19. A device as claimed in claim 18, wherein said two-colour LEDs (13) are powered pulse-wise.

20. A device as claimed in claim 1, wherein said indicating means (13) of acoustic type is a pulse-wise operated piezoelectric buzzer (33).

21. A device as claimed in claim 1, including a first compartment (15) housing said storage battery (2); a second compartment (16) within which there is provided a housing (3) which closes about said drip chamber (17) and in which said shutoff device (4) is housed; a third compartment (18) housing the electromagnet (5) with which the shutoff device (4) is provided, the sensor means (28, 29), the indicating means (13, 33) and the electronic circuit (12), such that all the components are assembled within a single container having dimensions such as to result in a small overall size of the device (1).

22. A device as claimed in claim 21, wherein said shutoff device (4) second lever (7) has one arm (19) shorter than another arm (20); a counteracting pin (22) which maintains one end (23) of the second lever (7) in the pre-loaded position; said first lever (6) having an end on which there acts the electromagnet (5), against which said electromagnet (5) is held under the thrust of said second spring (9); and a pushbutton (26) for resetting the shutoff device (4).

23. A device as claimed in claim 22, wherein said second lever (7) and first lever (6) are first class levers.

24. A device as claimed in claim 22, wherein a shorter arm (19) of said second lever (7) is substantially 7 mm in length.

25. A device as claimed in claim 22, wherein a longer arm (20) of the second lever (7) is at least substantially 16 mm in length.

26. A device as claimed in claim 25, wherein said shutoff device (4) can apply a force of at least 20 newtons to the tube (14).

27. A device as claimed in claim 22, wherein said electromagnet (5) is operated by at least two successive current pulses.

28. A device as claimed in claim 26, wherein when electric current passes through the electromagnet (5), an end (36) of the first lever (6) is moved by a rod (25) rigid with a moving core of the electromagnet (5), and with it there also moves the counteracting pin (22) to release the second lever (7), and end (32) of said second lever (7) throttles the tube (14) of the system.

29. A device as claimed in claim 28, including a permanent magnet (27) located at an end of the electromagnet (5) distant from an end from which the rod (25) travels outwards from said electromagnet (5), on termination of its return travel said rod (25) at least partially traversing said permanent magnet (27) so that said permanent magnet (27) causes the rod (25), rigid with the moving core of the electromagnet (5), to return to its initial position after the electromagnet (5) has operated.

30. A device as claimed in claim 28, including an idle travel portion before the action of the electromagnet (5) causes the rod (25) to strike the first lever (6) such that the rod (25) has a hammer effect on an end (36) of the first lever (6).

31. A device as claimed in claim 1, wherein the walls of the housing (3) are of dark and/or opaque color.

32. A device as claimed in claim 1, wherein said storage battery (2) includes at least one storage battery element rechargeable by means external to the device (1).

33. A device as claimed in claim 1, including a capacitor (37) which charges at the moment of activation of the device (1) and transfers energy to the electromagnet (5) should the consumed current be high in relation to the capacity of the storage battery (2).

34. A device for monitoring and controlling an intravenous infusion system (1) comprising:
    at least one electrical storage battery (2);
    a housing (3) adapted to be closed about a drip chamber (17) from which a tube (14) of the intravenous infusion system emerges;
    at least one geared motor (42) powered by direct current from the storage battery (2);

a cam (44) connected to the geared motor (42);

a lever (45) biased by a torsion spring (46);

electronic circuit means (12) comprising control means contained within at least one microcontroller means (40); sensor means (28, 29) for sensing droplets, generating droplet signals and transferring droplet signals to the microcontroller means (40) for either activating or not activating indicating means (13, 33); means for generating electrical signals for controlling the operation of the geared motor (42) such that said geared motor (42) acts, via the cam (44), on the lever (45) which consequently continuously regulates the opening and closing of the tube (14) and hence the rate of infusion of the solution to be administered.

35. A device as claimed in claim 34, wherein said electrical signals generating means includes a keypad and/or a bar code.

36. A device as claimed in claim 34, wherein said electrical signals generating means includes reader means defined by laser diodes.

37. A device as claimed in claim 34, wherein said lever (45) is a first class lever having a fulcrum (52) closer to the point of application of the force which throttles the tube (14) than a point of application of the force impressed by said cam (44).

38. A device as claimed in claim 34, wherein said lever (45) is provided with a protuberance (47) on which said cam (44) acts.

39. A device as claimed in claim 38, wherein said cam (44) engages the protuberance (47) of said lever (45).

40. A device as claimed in claim 34, wherein said electrical signals generating means includes a dedicated enabling means to prevent possible tampering and/or adjustment.

41. A device as claimed in claim 40, wherein said dedicated enabling means includes a pulse code.

42. A device as claimed in claim 40, wherein said dedicated enabling means includes a jack plug.

43. A device as claimed in claim 34, wherein said electronic circuit means (12) includes a memory device to maintain the data inserted into said electrical signals generating means.

* * * * *